US007001747B1

(12) United States Patent
Kellenberger et al.

(10) Patent No.: US 7,001,747 B1

(45) Date of Patent: Feb. 21, 2006

(54) NUCLEIC ACID MOLECULES ENCODING MODIFIED POLYKETIDE SYNTHASES CONTAINING POLYLINKERS AND USES THEREOF

(75) Inventors: Johannes Kellenberger, Basel (CH); Peter Francis Leadlay, Cambridge (GB); James Staunton, Cambridge (GB); Kim Jonelle Stutzman-Engwall, East Lyme, CT (US); Hamish Alastair Irvine McArthur, Mystic, CT (US)

(73) Assignees: Biotica Technology Limited, Cambridge (GB); Pfizer, Inc., New York, NY (US)

( * ) Notice: Subject to any disclaimer, the term of this patent is extended or adjusted under 35 U.S.C. 154(b) by 0 days.

(21) Appl. No.: 09/743,162

(22) PCT Filed: Jul. 6, 1999

(86) PCT No.: PCT/GB99/02158

§ 371 (c)(1), (2), (4) Date: Aug. 24, 2001

(87) PCT Pub. No.: WO00/01827

PCT Pub. Date: Jan. 13, 2000

(30) Foreign Application Priority Data

Jul. 6, 1998 (GB) .................................. 9814622

(51) Int. Cl.
*C12P 19/62* (2006.01)

(52) U.S. Cl. ...................... 435/76; 435/69.1; 435/183; 435/252.35; 435/252.3; 435/320.1; 435/91.4; 536/23.1; 536/23.2; 536/23.7

(58) Field of Classification Search ............... 536/23.1, 536/23.2, 23.7; 435/320.1, 252.3, 252.35, 435/91.4, 183, 69.1, 76
See application file for complete search history.

(56) References Cited

OTHER PUBLICATIONS

Elkmanns et al. A family of *Corynebacterium glutamicum/Escherichia coli* shuttle vectors for cloning, controlled gene expression, and promoter probing. Gene (1991) 102(1): 93-98.*

* cited by examiner

*Primary Examiner*—Kathleen M. Kerr
*Assistant Examiner*—Hope Robinson
(74) *Attorney, Agent, or Firm*—Dann, Dorfman, Herrell & Skillman, P.C.

(57) ABSTRACT

Nucleic acid molecules encoding at least part of a Type I polyketide synthase, and having a polylinker with multiple restriction enzyme sites in place of one or more PKS genes encoding enzymes associated with reduction, optionally further including nucleic acid incorporated into the polylinker, the further nucleic acid encoding one or more reductive enzymes; plasmids incorporating such nucleic acids; host cells transfected with such plasmids; methods relating thereto.

24 Claims, 13 Drawing Sheets

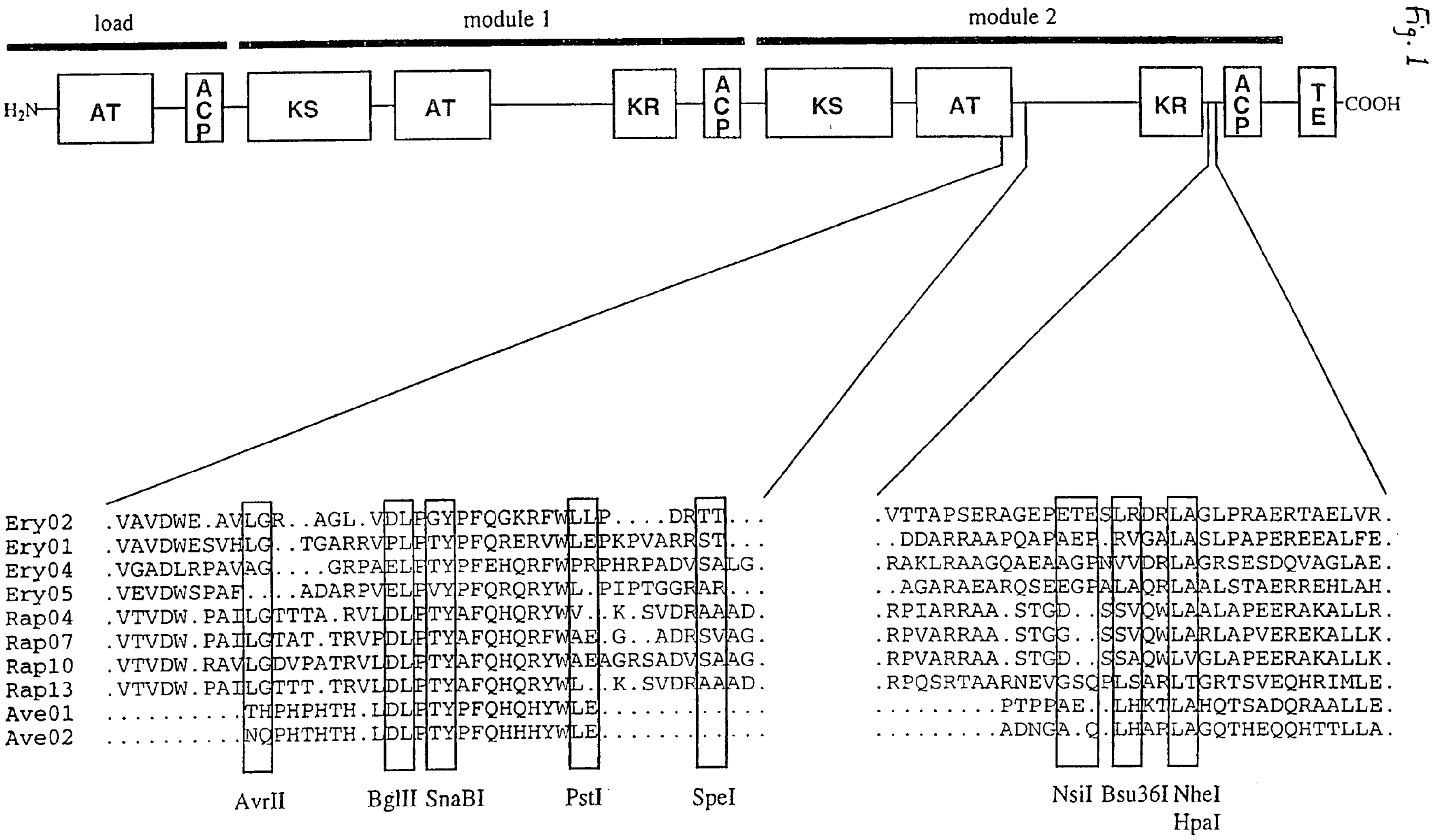
Fig. 1
load
module 1
module 2
$H_2N$
AT
ACP
KS
AT
KR
ACP
KS
AT
KR
ACP
TE
COOH
Ery02 .VAVDWE.AVLGR..AGL.VDLPGYPFQGKRFWLLP....DRTT... .VTTAPSERAGEPETESLRDRLAGLPRAERTAELVR.
Ery01 .VAVDWESVHLG..TGARRVPLPTYPFQRERVWLEPKPVARRST... ..DDARRAAPQAPAEP.RVGALASLPAPEREEALFE.
Ery04 .VGADLRPAVAG....GRPAELPTYPFEHQRFWPRPHRPADVSALG. .RAKLRAAGQAEAAGPNVVDRLAGRSESDQVAGLAE.
Ery05 .VEVDWSPAF....ADARPVELPVYPFQRQRYWL.PIPTGGRAR... ..AGARAEARQSEEGPALAQRLAALSTAERREHLAH.
Rap04 .VTVDW.PAILGTTTA.RVLDLPTYAFQHQRYWV..K.SVDRAAAD. .RPIARRAA.STGD..SSVQWLAALAPEERAKALLR.
Rap07 .VTVDW.PAILGTAT.TRVPDLPTYAFQHQRFWAE.G..ADRSVAG. .RPVARRAA.STGG..SSVQWLARLAPVEREKALLK.
Rap10 .VTVDW.RAVLGDVPATRVLDLPTYAFQHQRYWAEAGRSADVSAAG. .RPVARRAA.STGD..SSAQWLVGLAPEERAKALLK.
Rap13 .VTVDW.PAILGTTT.TRVLDLPTYAFQHQRYWL..K.SVDRAAAD. .RPQSRTAARNEVGSQPLSARLTGRTSVEQHRIMLE.
Ave01 ..........THPHPHTH.LDLPTYPFQHQHYWLE.......... .........PTPPAE..LHKTLAHQTSADQRAALLE.
Ave02 ..........NQPHTHTH.LDLPTYPFQHHHYWLE.......... .........ADNGA.Q.LHAPLAGQTHEQQHTTLLA.
AvrII
BglII SnaBI
PstI
SpeI
NsiI Bsu36I NheI
HpaI

Fig. 4 forward (P1f):

5'-CTA GGC CGG GCC GGA CTG GTA GAT CTG CCT ACG TAT CCT TTC CAG
GGC AAG CGG TTC TGG CTG CAG CCG GAC CGC ACT AGT CCT CGT GAC GAG
GGA GAT GCA TCG AGC CTG AGG GAC CGG TT-3' backward (P1b):

5'-AAC CGG TCC CTC AGG CTC GAT GCA TCT CCC TCG TCA CGA GGA CTA GTG
CGG TCC GGC TGC AGC CAG AAC CGC TTG CCC TGG AAA GGA TAC GTA
GGC AGA TCT ACC AGT CCG GCC CGG C-3' oligos annealed:

```
CTAGGCCGGGCCGGACTGGTAGATCTGCCTACGTATCCTTTCCAGGGCAAGCGGTTCTGGCTGCAG...
    CGGCCCGGCCTGACCATCTAGACGGATGCATAGGAAAGGTCCCGTTCGCCAAGACCGACGTC...
-----                   ------   ------                              ------
AvrII                   BglII    SnaBI                               PstI
```

```
...CCGGACCGCACTAGTCCTCGTGACGAGGGAGATGCATCGAGCCTGAGGGACCGGTT
...GGCCTGGCGTGATCAGGAGCACTGCTCCCTCTACGTAGCTCGGACTCCCTGGCCAA
           ------                   ------     -------     ---
           SpeI                     NsiI       Bsu36I      HpaI
```

Fig. 5b
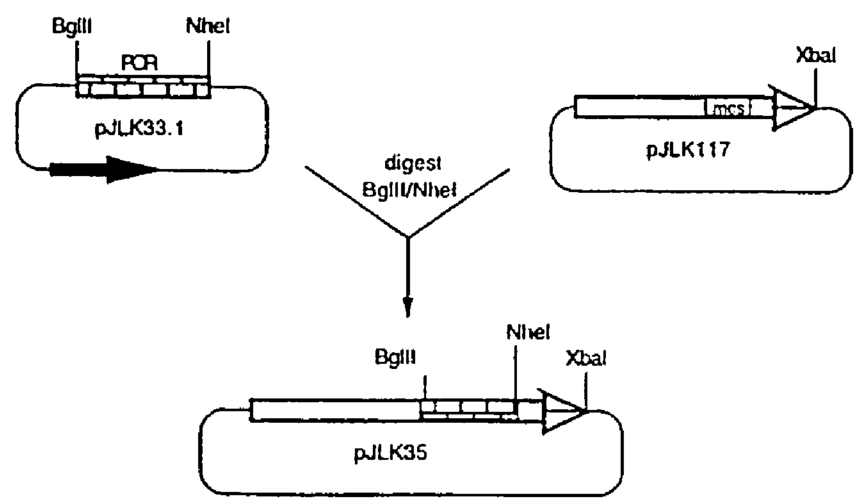
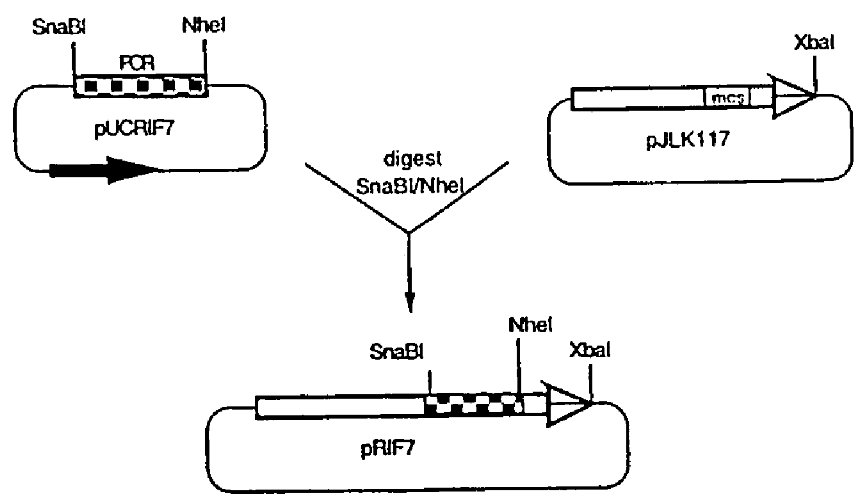

Fig. 7a

```
   1  CCCGGGCGAT CTCCCGGATC ACCTGTGCGG GGCTGGGCAT GTGCAGGAGA
  51  CACTCCAGGG CCCACGCCGC GTCGAAGGAC CCGTCGGGAA ACGGCAGTTC
 101  CATCGCGTCG GCACGGGTGA ACACGACCCG GTCCGCCACG TGCGACTGCT
 151  TCGCGAGAGC GGTCGCCAGC CCGACCTGAA CCTCGCTCAC CGTCACGCCG
 201  ACGACATCGA CGGGCGCGCT CAGGGCGAGC CGCACCGCCG GCTTTCCGGA
 251  ACCGCAGCCG ACGTCCAGGA CCCGGCGGCC CGTGATGCCT CTCAGCTTGC
 301  CGATGAGGAG ATCGGTGAGC CGGTCGGCGG CCTTGCCCGG TGAACTGCCG
 351  TCCCCCGGCT GCGGCCAGTA TCCGAGGTGG GTGTTCCCAC CCAGCGCACG
 401  ATTCATGAGG TCGGTCAAAC GGTCGTAGTA GTCCCCCACT TCCAGGGAAG
 451  AGGGCGGGGT CTGCTCCGGG ACGGCCATCA TGGTCGGGAA CCTCCGCAAT
 501  CCGGGCCGGG CGGCCCAGCT GTCGTGGCGA TCTACTCCAG GAAACGTCGA
 551  CCTTTTTCTG CCACTTGTCC GAGCTATGCA GACACCCCGA TCCCCTAAGA
 601  AATGAACACC CTTGGGAACG GCACAGCCCA GGGGTGGATA GGGGTATTCG
 651  CCGCCGCCGC GCCGTCATTA GCTTTGAAGA GTTGAAGACG TTCAAGACAT
 701  TGATGCCCGG CCGTCAGCGG ATTTCTCGCG CTCCTTTCAT TCTTCGACGC
 751  TGCATTGCAG CTCTCATCAT GTCCGCACGG CCGCCGAGCA TTGCCTAGCG
 801  GTGAGGACAC AGCTCAGGTG CAGAGGATGG ACGGCGGGGA AGAACCCCGC
 851  CCTGCGGCAG GGGAGGTCCT CGGAGTGGCC GACGAGGCGG ACGGCGGCGT
 901  CGTCTTCGTT TTTCCCGGGC AGGGCCCGCA ATGGCCGGGC ATGGGAAGGG
 951  AACTTCTCGA CGCTTCCGAC GTCTTCCGGG AGAGCGTCCG CGCCTGCGAA
1001  GCCGCGTTCG CGCCCTACGT CGACTGGTCG GTGGAGCAGG TGTTGCGGGA
1051  CTCGCCGGAC GCTCCCGGGC TGGACCGGGT GGACGTCGTC CAGCCGACCC
1101  TGTTCGCCGT CATGATCTCC CTGGCCGCCC TCTGGCGCTC GCAAGGGGTC
1151  GAGCCGTGCG CGGTGCTGGG ACACAGCCTG GGCGAGATCG CGGCAGCCCA
1201  CGTCTCGGGA GGCCTGTCCC TGGCCGACGC CGCACGCGTG GTGACGCTTT
1251  GGAGCCAGGC ACAGACCACC CTTGCCGGGA CCGGCGCGCT CGTCTCCGTC
1301  GCCGCCACGC CGGATGAGCT CCTGCCCCGA ATCGCTCCGT GGACCGAGGA
1351  CAACCCGGCG CGGCTCGCCG TCGCAGCCGT CAACGGACCC CGGAGCACAG
1401  TCGTTTCCGG TGCCCGCGAG GCCGTCGCGG ACCTGGTGGC CGACCTCACC
1451  GCCGCGCAGG TGCGCACGCG CATGATCCCG GTGGACGTTC CCGCCCACTC
1501  CCCCCTGATG TACGCCATCG AGGAACGGGT CGTCAGCGGC CTGCTGCCCA
1551  TCACCCCACG CCCCTCCCGC ATCCCCTTCC ACTCCTCGGT GACCGGCGGC
1601  CGCCTCGACA CCCGCGAGCT AGACGCGGCG TACTGGTACC GCAACATGTC
1651  GAGCACGGTC CGGTTCGAGC CCGCCGCCCG GCTGCTTCTG CAGCAGGGGC
1701  CCAAGACGTT CGTCGAGATG AGCCCGCACC CGGTGCTGAC CATGGGCCTC
1751  CAGGAGCTCG CCGCGGACCT GGGCGACACC ACCGGCACCG CCGACACCGT
1801  GATCATGGGC ACGCTGCGCC GCGGCCAGGG CACCCTGGAC CACTTCCTGA
1851  CGTCTCTCGC CCAACTACGG GGGCATGGTG AGACGTCGGC GACCACCGTC
1901  CTCTCGGCAC GCCTGACCGC GCTGTCCCCC ACGCAGCAGC AGTCGCTGCT
1951  CCTGGACCTG GTGCGCGCCC ACACCATGGC GGTGCTGAAC GACGACGGAA
2001  ACGAGCGCAC CGCGTCGGAT GCCGGCCCAT CGGCGAGTTT CGCCCACCTC
2051  GGCTTCGACT CCGTCATGGG TGTCGAACTG CGCAACCGCC TCAGCAAGGC
2101  CACGGGCCTG CGGTTGCCCG TGACGCTCAT CTTCGACCAC ACCACGCCGG
2151  CCGCGGTCGC CGCGCGCCTT CGGACCGCGG CGCTCGGCCA CCTCGACGAG
2201  GACACCGCGC CCGTACCGGA CTCACCCAGC GGCCACGGAG GCACGGCAGC
2251  GGCGGACGAC CCGATCGCCA TCATCGGCAT GGCATGCCGT TTCCCGGGCG
```

Fig. 7b

```
2301  GAGTCCGGTC CCCGAAGGAC CTGTGGGAGC TGCCCGCCTC GGGCGGAGAC
2351  GCCATCGGGC CGTTCCCCAC CGACCGCGGA TGGCCCACGG AACAGCGTCA
2401  CGCCCAGGAC CCCACGCAGC CCGGCACGTT CTATCCGCAG GGAGGCGGGT
2451  TCCTTCACGA CGCGGCGCAC TTCGACGCCG GCTTCTTCGG AATCAGTCCA
2501  CGTGAGGCAC TGGCGATGGA TCCGCAGCAG CGGCTGCTGC TGGAGACGTC
2551  CTGGGAGGCG TTCGAGCGGG CGGGAATCGA TCCGCTGTCG GTACGCGGGT
2601  CCCGTACGGG CGTCTTCGCG GGCGCCCTCT CCTTCGACTA CGGCCCGCGT
2651  ATGGACACCG CGTCGTCGGA GGGCGCCGCG GACGTGGAGG GCCACATCCT
2701  CACCGGTACC ACGGGCAGCG TCCTGTCGGG CCGTATCGCC TACAGCTTCG
2751  GGCTGGAAGG GCCGGCGATC ACCGTGGACA CGGGGTGCTC GGCATCGCTC
2801  GTGACGCTGC ATCTGGCGTG CCAGTCGCTG CGGTCGGGTG AGTGCACGCT
2851  CGCGCTGGCC GGCGGCGTCT CGGTCATGTC CACCCTCGGC ATGTTCATCG
2901  AGTTCTCCCG GCAGCGCGGG CTGTCGGTGG ACGGCAGGTG CAAGGCGTAC
2951  TCGGCTGCAG CCGACGGCAC CGGCTGGGGC GAGGGCGTCG GGATGCTGTT
3001  GGTGGAGCGG TTGTCGGATG CGGTGCGGCT GGGGCATCGG GTGCTGGCGG
3051  TGGTACGCGG CAGTGCGGTC AACCAGGACG GTGCGTCGAA TGGGCTGACG
3101  GCGCCGAACG GTCCGGCTCA GGAGCGGGTG ATCCGGCAGG CGTTGGCGAA
3151  CGCGGGGTTG TCCGTGGCGG ATGTGGATGT GGTGGAGGGG CACGGGACGG
3201  GCACGACGCT GGGTGATCCG ATCGAGGCAC AGGCGTTGCT CGCCACGTAC
3251  GGGCAGCGGG CCGGTGACAG GCCGCTGTGG CTGGGGTCTC TGAAGTCCAA
3301  CATCGGGCAC ACCATGGCTG CCGCGGGTGT GGGTGGGGTC ATCAAGATGG
3351  TGATGGCGTT GCGGGAGGGG GTGTTGCCGC GGACGTTGCA TGTGGATGAG
3401  CCGTCGCCGC AGGTGGACTG GTCCGCGGGG GCGGTGCGGC TGCTGACGGA
3451  GGCGGTGCCG TGGCCGGGGG ACGCGGCAGG GCGGTTGCGG CGGGCGGGAG
3501  TGTCGTCGTT CGGGATCGGC GGCACGAATG CGCATGTGAT TTTGGAGGAG
3551  GCGCCGGCGG CGGGGGGCTG TGTTGCCGGG GGTGGGGTGT TGGAGGGTGC
3601  TCCGGGTCTT GCCATTTCGG TGGCTGAGTC GGTGGCCGCT CCAGTGGCTG
3651  TGTCTGCGCC GGTGGCTGAG TCGGTGCCGG TGCCGGTGCC GGTGCCGGTT
3701  CCTGTGCCGG TGTCGGCTAG GTCTGAGGCT GGGTTGCGGG CGCAGGCGGA
3751  GGCGTTGCGT CAGTACGTGG CAGTCCGGCC GGACGTTTCG CTTGCCGATG
3801  TGGGTGCGGG TCTGGCCTGT GGGCGGGCTG TGCTGGAGCA TCGTGCGGTC
3851  GTCCTGGCCG CGGACCGTGA GGAGCTGGTG CAAGGGTTGG GGGCGCTGGC
3901  GGCGGGTGAG CCGGATCGGC GGGTGACCAC GGGTCATGCG CCGGGTGGTG
3951  ACCGGGGCGG TGTCGTCTTC GTGTTTCCCG GACAGGGTGG GCAGTGGGCC
4001  GGGATGGGTG TGCGTCTGCT CGCCTCCTCT CCGGTGTTCG CCCGGCGGAT
4051  GCAGGCGTGC GAGGAGGCTC TGGCGCCGTG GGTGGACTGG TCTGTGGTGG
4101  ACATCCTGCG CCGGGACGCG GGGGATGCGG TGTGGGAGCG GGCCGATGTG
4151  GTCCAGCCTG TGCTGTTCAG CGTCATGGTG TCTTTGGCTG CTCTGTGGCG
4201  TTCCTACGGT ATCGAACCCG ACGCGGTCCT TGGCCATTCC CAGGGCGAGA
4251  TCGCGGCCGC GCATGTGTGT GGGGCGCTGA GCCTGAAGGA CGCGGCGAAG
4301  ACTGTTGCGC TGCGCAGCCG GGCGCTGGCC GCTGTGCGGG GCCGGGGCGG
4351  CATGGCCTCA GTGCCGCTGC CTGCCCAGGA GGTGGAGCAG CTCATTGGTG
4401  AGCGGTGGGC GGGGCGGTTG TGGGTGGCGG CGGTCAACGG CCCCCGCTCC
4451  ACCGCCGTCT CGGGGGATGC CGAGGCGGTG GACGAGGTGC TGGCGTACTG
4501  TGCCGGCACC GGGGTGCGGG CCCGGCGGAT CCCGGTCGAC TATGCCTCGC
4551  ACTGCCCCCA TGTGCAGCCC CTGCGGGAGG AGTTGCTGGA GCTGCTGGGG
```

Fig. 7c

```
4601  GACATCAGCC CGCAGCCGTC CGGCGTGCCG TTCTTCTCCA CGGTGGAGGG
4651  CACCTGGCTG GACACCACAA CCCTGGACGC CGCCTACTGG TACCGCAACC
4701  TGCACCAGCC GGTCCGTTTC AGCGATGCCG TCCAGGCCCT GGCGGATGAC
4751  GGACACCGCG TCTTCGTCGA AGTCAGCCCC CACCCCACCC TCGTCCCCGC
4801  CATCGAAGAC ACCACCGAAG ACACCGCCGA AGACGTCACC GCGATCGGCA
4851  GCCTCCGCCG CGGCGACAAC GACACCCGCC GCTTCCTCAC CGCCCTCGCC
4901  CACACCCATA CCACCGGCAT CGGCACACCC ACCACCTGGC ACCACCACTA
4951  CACCCACCAC CACACCCACC CCCACCCCCA CACGCACCTC GACCTGCCCA
5001  CCTACCCCTT CCAACACCAG CACTACTGGC TCGAGAGCTC ACAGCCGGGT
5051  GCCGGATCCG GTTCGGGTGC CGGTGCCGGT TCGGGTGCCG GTTCCGGGCG
5101  GGCAGGGACT GCGGGCGGGA CGGCAGAGGT GGAGTCGCGG TTCTGGGACG
5151  CGGTGGCCCG CCAGGACCTG GAAACGGTCG CGACCACACT CGCCGTGCCC
5201  CCCTCCGCCG GCCTGGACAC GGTGGTGCCC GCACTCTCCG CCTGGCACCG
5251  CCACCAACAC GACCAAGCCC GCATCAACAC CTGGACCTAC CAGGAAACCT
5301  GGAAACCCCT CACCCTCCCC ACCACCCACC AACCCCACCA AACCTGGCTC
5351  ATCGCCATCC CCGAAACCCA GACCCACCAC CCCCACATCA CCAACATCCT
5401  CACCAACCTC CACCACCACG GCATCACCCC CATCCCCCTC ACCCTCAACC
5451  ACACCCACAC CAACCCCCAA CACCTCCACC ACACCCTCCA CCACACCCGA
5501  CAACAAGCCC AAAACCACAC CACCGGAGCC ATCACCGGCC TGCTCTCCCT
5551  CCTCGCCCTC GACGAAACAC CCCACCCCCA CCACCCCCAC ACACCCACCG
5601  GCACCCTCCT CAACCTCACC CTCACCCAAA CCCACACCCA AACCCACCCA
5651  CCAACCCCCC TCTGGTACGC CACCACCAAC GCCACCACCA CCCACCCCAA
5701  CGACCCCCTC ACACACCCCA CCCAAGCCCA AACCTGGGGA CTCGCCCGCA
5751  CCACCCTCCT CGAACACCCC ACCCACACCG CCGGAATCAT CGACCTCCCC
5801  ACCACCCCCA CCCCCCACAC CCTCCACCAC CTCACCCAAA CCCTCACCCA
5851  ACCCCACCAC CAAACCCAAC TCGCCATCCG CACCACCGGC ACCCACACCC
5901  GCCGCCTCAC CCCCACCACC CTCACCCCCA CACACCAACC ACCCACCCCC
5951  ACCCCCCACG GAACCACCCT CATCACCGGC GGAACCGGCG CCCTCGCCAC
6001  CCACCTCACC CACCACCTCA CCACCCACCA ACCCACCCAA CACCTCCTCC
6051  TCACCAGCCG AACCGGCCCC CACACCCCCC ACGCACAACA CCTCACCACC
6101  CAACTCCAAC AAAAAGGCAT CCACCTCACC ATCACCACCT GCGACACCAG
6151  CAACCCAGAC CAACTCCAAC ATCTCCTCAA CACCATCCCC CCACAACACC
6201  CCCTCACCAC CGTCATCCAC ACCGCAGGCA TCCTCGACGA CGCCACCCTC
6251  ACCAACCTCA CCCCCACCCA ACTCAACAAC GTCCTCCGCG CCAAAGCCCA
6301  CAGCGCCCAC CTCCTCCACC AACTCACCCA ACACACCCCC CTCACCGCCT
6351  TCGTCCTCTA CTCCTCCGCC GCCGCCACCT TCGGCGCACC CGGCCAAGCC
6401  AACTACGCCG CAGCCAACGC CTACCTCGAC GCCCTCGCCC ACCACCGCCA
6451  CACCCACCAC CTCCCCGCCA CCAGCATCGC CTGGGGCACC TGGCAAGGAA
6501  ACGGACTCGC TGATTCGGAC AAGGCCCGCG CATATCTCGA CCGCCGCGGG
6551  TTTCGACCCA TGTCACCCGA GTTGGCCACG GCAGCGGTCA CGCAGGCGAT
6601  CGCGGACACC GAACGGCCGT ATGTCGTCAT CGCCGACATC GACTGGAGCA
6651  AGATCGAACA CACCTCTCAG ACCAGCGACC TGGTGAGCGC GGCCCGGGAA
6701  AGGGAGCCAG CTGTCCAGCG CCCCACTCCA CCGGCGGAGT TGCACAAAAC
6751  GCTGGCCCAT CAGACGTCGG CCGACCAACG GGCCGCATTG CTCGAGCTCG
6801  TACGAGACCA TGTGGCGGCA GTGCTCCGGC ACGCGGACCC GAAAGCCATC
6851  GCGCCCGACC AGTCGTTCCG TGCACTCGGC TTCGATTCAC TCACGGCCGT
```

Fig. 7d

```
6901  CGAGTTCCGA AACCTGCTGA TCAAGGCAAC AGGACTCCGC CTTCCTGTCT
6951  CGCTGGTCTT CGACCACCCG ACCCCTGCCA AACTCGCCGT ACACCTGCAG
7001  AACCAACTGC GGGGCACAGC AGCGGAGTCG GCTCCTTCAG CGGCAGCCGT
7051  TACCGCCGAG GCTTCTGTCA CCGAGCCGAT CGCCATCGTT GGCATGGCCT
7101  GTCGTTTCCC CGGCGGAGTG ACCTCGGCGG ACGACTTCTG GGATCTGATC
7151  TCCTCCGAGC AGGACGCGAT CGGCGGATTC CCCACCGACC GCGGCTGGGA
7201  CCTGGACACG CTCTACGACC CCGACCCCGA CCACCCCGGC ACCTGCTACA
7251  CCCGAAACGG CGGATTCCTC TACGACGCAG GCCACTTCGA CGCCGAATTC
7301  TTCGGCATCA GCCCCCGCGA AGCCCTCGCC ATGGACCCCC AGCAACGACT
7351  CCTCCTCGAA ACCGCCTGGG AAACCATCGA ACACGCCGGC ATCAACCCCC
7401  ACACCCTCCA CGGCACCCCC ACCGGAGTCT TCACCGGCAC CAACGGACAG
7451  GACTACGCAC TTCGCGTGCA CAACGCGGGC CAGTCAACCG ATGGTTTCGC
7501  ACTGACCGGA ACCGCCGGCA GCGTCATCTC CGGTCGTATC TCGTACACGT
7551  TTGGTTTTGA GGGTCCTGCG GTGTCGGTGG ACACGGCTTG TTCCTCGTCG
7601  TTGGTGGCTT TGCATCTGGC CTGTCAGGCG TTGCGTGCGG GTGAGTGCTC
7651  GATGGCGCTT GCCGGGGGTG TGACGGTGAT GTCGTCTCCG GGTGCCTTCG
7701  TGGAGTTTTC GCGGCAGCGG GGTCTGGCCG CGGACGGGCA TTGCAAGGCG
7751  TTCTCGGCGG CGGCGGACGG GACCGGCTGG GGTGAGGGTG TGGGGATGCT
7801  GCTGGTGGAG CGGCTCTCCG ACGCCCATCG CAACGGTCAC CGTGTCCTGG
7851  CCGTGGTGCG TGGCAGTGCG GTCAACCAGG ACGGTGCGAG CAACGGTCTG
7901  ACCGCGCCCA ACGGGCCGTC CCAGCAGCGT GTCATCCGCC AGGCCCTCGC
7951  CAACGCCGGC TTGTCGGCCG GTGATGTCGA CGCGGTGGAG GCCCACGGCA
8001  CCGGCACCAC TTTGGGCGAC CCGATCGAGG CCCAGGCCCT CCTCGCGACC
8051  TACGGACAGG ACCGTGCCGG CGAGGGGCCG CTGTGGCTGG GCTCGGTCAA
8101  GTCCAATGTC GGTCACACAC AGGCTGCCGC GGGCGTCGCC GGGGTGATCA
8151  AGATGGTGAT GGCGCTGCGG CATGGTCTGC TGCCGCGGAC GTTGCATGTG
8201  GATGAGCCGT CGCCGCATGT GGACTGGTCC GCGGGTGCGG TGCAGCTGCT
8251  GACGGAGACG GTGCCCTGGC CCGGCGGGGA GGGGCGGCTA CGGCGGGCAG
8301  GAGTGTCATC ATTCGGCGTC AGCGGCACCA ACGCCCACGT CATCCTCGAA
8351  GAAGCACCCG CCGACGACGT TCCGGGGGGA CCACCCGCCG GCGAGGGTGA
8401  CGCGGGCAGC GACGATGAGG CTGCTGCCGG CAGTCCTGGG GTGTGGCCGT
8451  GGCTGGTGTC GGCCAAGTCG CAGCCGGCCC TGCGCGCCCA GGCCCAGGCC
8501  CTGCACGCCC ACCTCACCGA CCACCCCGGC CTCGACCTCG CGGATGTCGG
8551  ATACACCCTC GCCCACGCCC GCGCCGTGTT CGACCACCGC GCCACCCTCA
8601  TCGCCGCGGA CCGCGACACG TTCCTGCAAG CACTCCAGGC ACTCGCCGCA
8651  GGCGAGCCCC ACCCCGCCGT CATCCACAGC AGCGCCCCGG GCGGGACCGG
8701  GACCGGGGAG GCCGCAGGAA AGACCGCATT CATCTGCTCC GGACAGGGCA
8751  CCCAACGCCC CGGCATGGCC CACGGCCTCT ACCACACCCA CCCCGTCTTC
8801  GCCGCCGCAC TCAACGACAT CTGCACCCAC CTCGACCCCC ACCTCGACCA
8851  CCCCCTCCTC CCCCTCCTCA CCCAAAACGA CAACGACAAC GAGGACGCGG
8901  CCGCACTGCT CCAGCAGACC CGCTACGCCC AGCCCGCCCT CTTCGCCTTC
8951  CAGGTCGCCC TCCACCGCCT CCTCACCGAC GGCTACCACA TCACCCCCCA
9001  CTACTACGCC GGACACTCCC TCGGCGAAAT CACCGCCGCC CACCTCGCCG
9051  GCATCCTCAC CCTCACCGAC GCCACCACCC TCATCACCCA ACGCGCCACC
9101  CTCATGCAAA CCATGCCCCC CGGCACCATG ACCACCCTCC ACACCACCCC
9151  CCACCACATC ACCCACCACC TCACCGCCCA CGAAAACGAC CTCGCCATCG
```

Fig. 7e

```
 9201 CCGCCATCAA CACCCCCACC TCCCTCGTCA TCAGCGGCAC CCCCCACACC
 9251 GTCCAACACA TCACCACCCT CTGCCAACAA CAAGGCATCA AAACCAAAAC
 9301 CCTCCCCACC AACCACGCCT TCCACTCCCC CCACACCAAC CCCATCCTCA
 9351 ACCAACTCCA CCAGCACACC CAAACCCTCA CCTACCACCC ACCCCACACC
 9401 CCCCTCATCA CCGACAACAC CCCACCCGAC CAACTCCTCA CCCCCCACTA
 9451 CTGGACCCAA CAAGCCCGCA ACACCGTCGA CTACGCCACC ACCACCCAAA
 9501 CCCTCCACCA ACACGGCGTC ACCACCTACA TCGATCTCGG ACCCGACAAC
 9551 ACCCTCACCA CCCTCACCCA CCACAACCTC CCCAACACCC CCACCACCAC
 9601 CCTCACCCTC ACCCACCCCC ACCACCACCC CCAAACCCAC CTCCTCACCA
 9651 ACCTCGCCAA AACCACCACC ACCTGGCACC CCCACCACTA CACCCACCAC
 9701 CACAACCAAC CCCACACCCA CACCCACCTC GACCTCCCCA CCTACCCCTT
 9751 CCAACACCAC CACTACTGGC TCGAAAGCAC ACAGCCCGGT GCCGGCAACG
 9801 TGTCAGCAGC CGGACTCGAC CCCACCGAAC ACCCCCTACT CGGCGCCACA
 9851 TTGGAACTGG CGACTGACGG TGGAGCGCTT CTTGCAGGGC GCTTGTCTTT
 9901 GAGGTCGCAT CCGTGGCTGG CTGACCATGC CGTCGGCGGC ACGGTGCTGC
 9951 TGTCGGGCGC CACCTTCCTC GAACTCGCCC TTCATGCGGG CACATACGTG
10001 GGCTGCGACC GAGTGGATGA GCTGACGCTG CATGCGCCGC TGGTGGTTCC
10051 TGTGGATGGG GGTGTGAGTG TGCAGGTTGG GGTTGCGGCT GCGGATGGGG
10101 AGGGGCGGCG TTTGGTGAGT GTGTATGCGC GGGGTGGGAG TGCTTGTGGT
10151 GGGGGTGGTG CGTCGGGTGG GGTGTGGACG TGTCATGCCT CGGGGGTGCT
10201 GGTTGAGGCT GCTGCTGGTG GTGTGGTGGT GGATGGTCTG GCGGGGGTGT
10251 GGCCGCCGCG GGGTGCGGTG GCGGTGGATG TCGATGGTGT CCGTGACCGT
10301 TTGGCTGGGG CTGGTTGTGT TTTGGGGCCG GTGTTTTCGG GGCTGCGTGC
10351 GGTGTGGCGT GATGGGGGGG ATTTGCTGGC TGAGGTGTGT CTGCCGGAGG
10401 AGGCGTGGGG TGATGCGGCT GGTTTTGGGC TGCATCCGGC GTTGCTGGAT
10451 GGTGTGGTCC AGCCGTTGTC GGTGTTGCTT CCGGGTGGGA CGGGGTTTGG
10501 GGAGGGGGCG GGGTTCGGGG AGGGTGTTCG GGTGCCGGCT GTGTGGGGTG
10551 GTGTGTCGCT TCACCGGGCG GGTGTGACCG GTGTGCGGGT GCGTGTGTCG
10601 GCTGTCGGGC GGGGCGGCGG GCGTGAGGCG GTGTCGGTCG TGGTCGGGGA
10651 TGAGGCGGGT GTGCCGGTGG CGTCGGTCGA TCGTCTTGAG TTGCGGCCTG
10701 TGGATATGGG TCAGTTGCGT GCTGTCTCGG TTTCGGCGGG GCGGCGGGGT
10751 TCGCTGTATG CGGTGCAGTG GGCTGAGGTG GGTCCTGTGC CGGTGTGTGG
10801 GCAGGCGTGG GCGTGGCACG AGGACGTGGG TGAGAGCGGT GGTGGGCCTG
10851 TGCCGGGGGT GGTGGTGTTG CGGTGCCCGG ATGCCGGTGC CGGTGGCGGT
10901 GGCGGTGGCG GTGGTGGCGG TGGTGTGGGT GAGGTTGTTG GTGGGGTGTT
10951 GGGTGTGGTG CAGGGGTGGC TGGGGCTGGA GCGGTTTGCG GGTTCGCGGC
11001 TGGTGGTGGT GACCCGGGGT GCGGTGGTGG CCGGCCCGGA GGACGGCCCG
11051 GTGGATGTGG TGGGTGCGTC GGTGTGGGGG CTGGTGCGTT CGGCGCAGGC
11101 TGAGCATCCG GACCGGTTTG TCCTCCTCGA CCTCGACACC GACACCGGCA
11151 CCGACCTCGA CACCGGTGCT GGTGCTGGTT GGGGCGTGGA TGGTGGGCGT
11201 GTGGCGGCGG TGGTGGCGTG TGGTGAGCCG CAGTTGGCGG TGCGTGGGGA
11251 GCGGTTGCTG GCCGCACGCC TGACACGACT TGAGTCATCC GGTGATGTTC
11301 CAGCCCAGCG GTCCGGTGAC ACACGAGCCC GGCGGTCCGA CGTGCCTGCC
11351 CAGCGCTCCG GTGGCGTGCC TGCTCGGCGG TCGGTTGATG TATCGGGTCG
11401 GGAGGTGTTG CCGTGGTTGT CGGGTGGGTC GGTGTTGGTG ACGGGTGGGA
11451 CGGGTGTGCT GGGTGCGGCG GTGGCGCGGC ATCTGGCTGG TGTGTGTGGG
```

Fig. 7f

```
11501 GTGCGGGATC TGCTGTTGGT GAGCCGGCGT GGTCCGGATG CTCCGGGTGC
11551 GGAGGGTCTG CGGGCGGAGC TGGCCGCGTT GGGGGCGGAG GTGCGGATTG
11601 TTGCGTGTGA TGTGGGGGAG CGGCGGGAGG TGGTCCGGCT GCTGGAGGGT
11651 GTTCCTGCCG GGTGTCCGCT GACGGGTGTC GTGCATGCGG CTGGTGTGCT
11701 GGACGATGCG ACGATCGCCT CTCTCACGCC CGAGCGGCTG GGCACGGTGT
11751 TCGCGGCCAA GGTGGATGCC GCTCTTTTGC TGGATGAGCT GACGCGGGGT
11801 ATGGAGCTGT CGGCGTTCGT GCTGTTCTCC TCGGCCGCGG GGATCCTGGG
11851 GTCGGCCGGG CAGGGCAACT ACGCCGCGGC CAATGCCGCT CTGGACGCGC
11901 TGGCGTACCG GCGGCGGGCG GCGGGTCTGC CGGGGGTGTC GCTGGCGTGG
11951 GGGCTGTGGG AAGAGGCCAG CGGGATGACC GGGCACCTGG CCGGCACCGA
12001 CCACCGGCGC ATCATCCGTT CCGGTCTGCA TCCCATGTCG ACCCCGGACG
12051 CACTGGCCCT CTTCGATGCG GCCCTGGCTC TGGACCGGCC GGTCCTGCTG
12101 CCCGCCGACC TGCGTCCCGC CCCGCCCCTG CCGCCCCTGC TGCAGGACCT
12151 CCTGCCCGCC ACCCGCCGCC GCACCACCCG CACCACCACT ACCGGTGGTG
12201 CGGACAACGG CGCCCAGCTG CACGCCCGGC TGGCCGGCCA GACACACGAA
12251 CAACAGCACA CCACCCTCCT CGCCCTGGTC CGCTCCCACA TCGCCACCGT
12301 CCTGGGCCAC ACCACCCCCG ACACCATCCC CCCCGACCGC GCGTTCCGCG
12351 ACCTCGGCTT CGACTCCCTC ACCGCCGTCG A
```

NUCLEIC ACID MOLECULES ENCODING MODIFIED POLYKETIDE SYNTHASES CONTAINING POLYLINKERS AND USES THEREOF

This Application is a 371 of PCT/GB 9902158, filed on Jul. 6, 1999 which claims benefit under 35 U.S.C. 119 (a–d) to UK 9814622.8, filed on Jul. 6, 1998.

The present invention relates to polyketides, their preparation, and materials for use therein.

Polyketides are a large and structurally diverse class of natural products that includes many compounds possessing antibiotic or other pharmacological properties, such as erythromycin, tetracyclines, rapamycin, avermectin, polyether ionophores, and FK506.

In particular, polyketides are abundantly produced by *Streptomyces* and related actinomycete bacteria. They are synthesised by the repeated stepwise condensation of acylthioesters in a manner analogous to that of fatty acid biosynthesis. The greater structural diversity found among natural polyketides arises from the selection of (usually) acetate or propionate as "starter" or "extender" units; and from the differing degree of processing of the β-keto group observed after each condensation. Examples of processing steps include reduction to β-hydroxyacyl-, reduction followed by dehydration to 2-enoyl-, and complete reduction to the saturated acylthioester. The stereochemical outcome of these processing steps is also specified for each cycle of chain extension.

The biosynthesis of polyketides is initiated by a group of chain-forming enzymes known as polyketide synthases (PKSs). Two classes of polyketide synthase have been described in actinomycetes. However the novel polyketides and processes which are the subject of the present invention relate mainly to Type I PKSs, represented by the PKSs for the macrolides erythromycin, rapamycin and avermectin. Type I PKSs contain a different set or "module" of enzymes for each cycle of polyketide chain extension (Cortes, J. et al. Nature (1990) 348:176–178; Donadio, S. et al. Science (1991) 252:675–679; MacNeil, D. J. et al. Gene (1991) 115:119–125; Schwecke, T. et al. Proc. Natl. Acad. Sci. USA (1995) 92:7839–7843 and see e.g. FIG. 1 herein, or FIGS. 2a and 3 of WO98/01546); whereas Type II PKSs are represented by the synthases for aromatic compounds and contain only a single set of enzymatic activities for chain extension. These are re-used as appropriate in successive cycles.

A complete module dictating full reduction contains a ketoacyl-ACP synthase (KS) domain; an acyl carrier protein domain (ACP); an acyl-CoA:ACP acyltransferase (AT) for loading of the extender unit; and a ketoreductase (KR), a dehydratase (DH) and an enoylreductase (ER) domain for accomplishment of the processing of the β-keto group. Since these domains have enzymic activity, they may also be referred to herein as "enzymes", though this is not intended to imply anything about their structural relationship to other PKS domains. Similarly, the nucleic acid sequences encoding such domains may also be referred to as "genes", though this is not intended to imply anything about the presence or otherwise of separate regulatory regions for the different domains of a PKS.

The present invention particularly relates to processes for preparing polyketides by replacing the reductive loop (the segment from the end of the AT to the beginning of the ACP comprising either a KR or a KR and a DH or a KR, a DH and a ER) in a selected module of a Type I polyketide synthase gene cluster by the equivalent segment from the same or from a different PKS gene cluster, or by a mutated or synthetic segment, thereby generating new hybrid polyketide synthases that produce polyketides with different extent of reduction and/or stereochemistry in a predictable way.

For the avoidance of doubt, the term "extension module", as used hereinafter, refers to a set of domains of a Type I PKS, each having enzymic activity, which participate in one cycle of polyketide chain extension. More particularly, an extension module comprises KS, AT, a reductive loop (comprising one or more of KR, DH and ER), and ACP.

Rarely, the reductive loop may include other domains. For example yersiniabacter, which possesses a mixed PKS and polypeptide synthase, possesses a methyl transferase domain.

It has been reported that replacement of the reductive loop of module 2 in DEBS1TE with the equivalent segment of module 3 of the (Type I) erythromycin PKS gene yields a triketide ketolactone when expressed in *S. coelicolor* CH999 (Bedford, D. et al. Chemistry and Biology (1996) 3:827–831).

Similarly, replacement of the reductive loop of module 2 in DEBS1TE with the equivalent segment of module 5 of the erythromycin PKS yields a triketide lactone with the predicted structure and stereochemistry when expressed in *S. coelicolor* CH999 (McDaniel, R. et al. Chemistry and Biology (1997) 4:667–674). On the contrary, when the same experiment was carried out using the reductive loop of module 6 of the erythromycin PKS only a ketolactone could be isolated (McDaniel, R. et al. Chemistry and Biology (1997) 4:667–674).

In a further experiment it has been shown, that the reductive loop of module 2 in a trimodular system comprising the loading domain, the first, second and third extension module and the TE of the ery gene can also be substituted by the equivalent segment of module 4 of the rapamycin PKS comprising a KR and DH domain yielding a tetraketide with the predicted double bond when expressed in *S. coelicolor* CH999 (McDaniel, R. et al. J. Am. Chem. Soc. (1997) 119:4309–4310). In the same system the reductive loop of module 2 has been replaced by the equivalent segment of module 1 of the rapamycin PKS comprising a KR a DH and a ER domain yielding a tetraketide with the predicted oxidation level at C-5 when expressed in *S. coelicolor* CH999 (Kao, C. M. et al. J. Am. Chem. Soc. (1997) 119:11339–11340). On the contrary, when using the corresponding segment of module 4 of the erythromycin PKS gene only a polyketide with a double bond at the relevant position could be observed and not, as one would predict, full reduction (Kao, C. M. et al. J. Am. Chem. Soc. (1997) 119:11339–11340).

In two similar experiments the reductive loop of module 2 in the trimodular system has been substituted by the corresponding segment of module 2 of the rapamycin PKS containing a KR and an inactive DH domain and by the KR domain of module 4 of the rap PKS (the reductive loop of rap module 4 contains a KR and a DH domain). Both constructs are reported to yield a triketide lactone with a different stereochemistry at C-3 (Kao, C. M. et al. J. Am. Chem. Soc. (1998) 120:2478–2479).

In all the examples described above the same restriction sites, PstI and XbaI, have been used to join the DNA fragments (the location of the PstI site is identical to the PstI site used in the system described below and the XbaI site is in the same place as the Bsu36I site).

A model has been proposed for the structure of the DEB synthase, where the reductive domains form a loop which lies outside the core formed by the KS, AT and the ACP domains (Staunton et al. Nature structural biology (1996) 3:188–192). In addition it has been found that DEBS1 is hydrolysed by proteolytic enzymes at specific locations which mark the boundaries of the domains (Aparicio, J. F. et al. J. Biol. Chem. (1994) 269: 8524–8528). These proteolytic sites are found mainly in linker regions and it seems therefore ideal to join the fragments in close neighbourhood to these sites. Examples of this are documented in WO98/01546.

In one aspect the invention provides nucleic acid (particularly DNA) encoding at least part of a Type I polyketide synthase (PKS), said part comprising at least part of an extension module, wherein the nucleic acid has a polylinker with multiple restriction enzyme sites in place of one or more genes encoding enzymes associated with reduction.

In another aspect the invention provides nucleic acid (particularly DNA) encoding at least part of a Type I polyketide synthase, said part comprising at least part of an extension module, wherein the nucleic acid has a polylinker with multiple restriction enzyme sites which connects nucleic acid encoding (at least part of) AT to nucleic acid encoding (at least part of) ACP.

Such nucleic acids may have an additional nucleic acid, which encodes one or more reductive enzymes, inserted into the polylinker as described in more detail below. Such insertion is preferably performed following digestion of the polylinker-containing nucleic acids by two restriction enzymes. In order to provide a choice of insertion sites, the polylinker preferably includes at least three restriction sites, more preferably at least four, and further preferably at least six or eight restriction sites.

The polylinker may be provided by introducing exogenous (usually synthetic) nucleic acid into the Type I PKS-encoding nucleic acid, or may be provided by engineering the existing sequence of the Type I PKS-encoding nucleic acid. For example, to achieve the latter, restriction sites may be engineered (e.g. by site-directed mutagenesis) into sequences up- and/or downstream (preferably both) of where the absent reductive enzyme-encoding sequence would normally lie, particularly into sequences which encode polypeptide linkers between the reductive enzyme(s) and adjacent domains.

The polylinker desirably includes at least some of the following restriction sites: AvrII, BglII; SnaBI; PstI; SpeI; NsiI; Bsu36l; NheI; and HpaI. More desirably the polylinker includes at least four of these sites.

Preferably at least some of the restriction sites included in the polylinker are absent from the remainder of the nucleic acid into which it is incorporated. Desirably at least some of the sites included in the polylinker are uncommon in or absent from naturally occurring nucleic acid sequences which encode reductive enzymes of other (preferably Type I) PKSs. Desirably at least two of the sites are absent from at least about half, more desirably at least about three quarters, of known nucleic acid sequences encoding reductive enzymes of PKSs. Preferably the restriction sites are rich in A and T residues, since PKS genes tend to be rich in G and C residues.

Desirably the nucleic acids of the invention encode a loading module and/or one or more extension modules.

In another aspect the invention provides nucleic acid generally as indicated above but having further nucleic acid encoding one or more reductive enzymes (e.g. KR and/or DH and/or ER) inserted into the polylinker. The inserted nucleic acid may encode one or more reductive enzymes of the same polyketide synthase as that of the nucleic acid into which the polylinker is inserted, but from a different extension module. Alternatively the inserted nucleic acid may be exogenous, encoding one or more reductive enzymes from a different natural PKS or fatty acid synthase, or may be synthetic or may be mutated from a naturally occurring nucleic acid which encodes one or more reductive enzymes of a PKS or fatty acid synthase. Preferably, the inserted nucleic acid encodes one or more reductive enzymes from the same or another Type I PKS or fatty acid synthase, but alternatively it may encode one or more reductive enzymes from a Type II PKS or fatty acid synthase.

The genes encoding numerous examples of Type I PKSs have been sequenced and these sequences disclosed in publicly available DNA and protein sequence databases including Genbank, EMBL, and Swissprot. For example the sequences are available for the PKSs governing the synthesis of, respectively, erythromycin (Cortes, J. et al. Nature (1990) 348: 176–178; accession number X62569, Donadio, S. et al. Science (1991) 252: 675–679; accession number M63677); rapamycin (Schwecke, T. et al. Proc. Natl. Acad. Sci. USA (1995) 92: 7839–7843; accession number X86780); rifamycin (August et al. (1998); accession number AF040570); and tylosin (Eli Lily, accession number U78289), among others. Furthermore, FIG. 7 (SEQ ID NO: 1) herein shows the nucleic acid sequence encoding the first two modules of the avermectin PKS from *S. avermitilis*; this may be used as an alternative source for the inserts used in certain of the examples.

It is apparent to those skilled in the art that the overall sequence similarity between the nucleic acids encoding comparable domains or modules of different Type I PKSs is sufficiently high, and the domain organisation of different Type I PKSs so consistent between different polyketide-producing microorganisms, that the processes for obtaining novel hybrid polyketides described in the present invention will be generally applicable to all natural modular Type I PKSs or their derivatives.

In further aspects, the present invention provides vectors, such as plasmids or phages (preferably plasmids), including nucleic acids as defined in the above aspects and host cells (particularly of *Streptomyces* species) transfected with such nucleic acids or constructs.

In a still further aspect, the present invention provides polyketide synthases expressible by host cells as defined above. Such polyketide synthases may if desired be isolated from the host cells by routine methods, though it is usually preferable not to do so.

In further aspects the invention provides methods of creating novel functional PKS's and nucleic acids encoding them by means of insertion of nucleic acid encoding reductive enzymes into polylinkers as indicated above; and novel polyketides as produced by such PKS's. In a still further aspect, the present invention provides novel processes for the specific or preferential production of particular polyketides, using the materials and methods as defined in previous aspects. For example, the present invention provides processes for the generation by direct fermentation of C22–C23 dihydroavermectins, such as ivermectin (see e.g. Examples 25 and 26), and of B1 avermectins substantially free of B2 avermectins (see e.g. Examples 27 and 28).

In another aspect, the present invention provides novel polyketides and novel stereoisomers of polyketides, such as particular polyketides produced in accordance with one a or more of the Examples.

BRIEF DESCRIPTION OF THE FIGURES

FIG. 1 is a schematic drawing showing the location of restriction sites in type I polyketide synthase modules in regions of high homology in erythromycin module 2 (Ery02: SEQ ID NOs 36 and 37) erythromycin module 1 (Ery01: SEQ ID NOs 38 and 39), erythromycin module 4 (Ery04: SEQ ID NOs 40 and 41), erythromycin module 5 (Ery05: SEQ ID NOs 42 and 43), rapamycin module 4 (Rap04: SEQ ID NOs 44 and 45), rapamycin module 7 (Rap07: SEQ ID NOs: 46 and 47), rapamycin module 10 (Rap10: SEQ ID NOs 48 and 49), rapamycin module 13 (Rap13: SEQ ID NOs 50 and 51), avermectin module 1 (Ave01: SEQ ID NOs 52 and 53) and avermectin module 2 (Ave02: SEQ ID NOs 54 and 55).

FIG. 4 provides the oligonucleotide sequences (Plf—SEQ ID NO: 56 and Plb—SEQ ID NO: 57) used to construct the polylinker in pJLK114, and the annealed oligonucleotide construct (SEQ ID NOs 58–61).

FIG. 5*b* is a flow chart depicting the construction of pJLK35 and pRIF7.

FIGS. 7*a*–7*f* are the nucleotide sequence of the first two modules of the avermectin PKS from S avermitilis (SEQ ID NO: 1).

In order to enable the exchange of the reductive loop in module 2 of the erythromycin PKS gene in the DEBSlTE system (Cortes J. et al. (1995) 268:1487–1489) a polylinker (multiple cloning site (mcs)) has been inserted in place of the reductive loop of module 2 thereby generating a minimal module comprising a KS, an AT and an ACP. (This system is still functional and produces a ketolactone (see examples 2 and 4).) The mcs contains unique recognition sites for 9 restriction enzymes.

Figure 2:
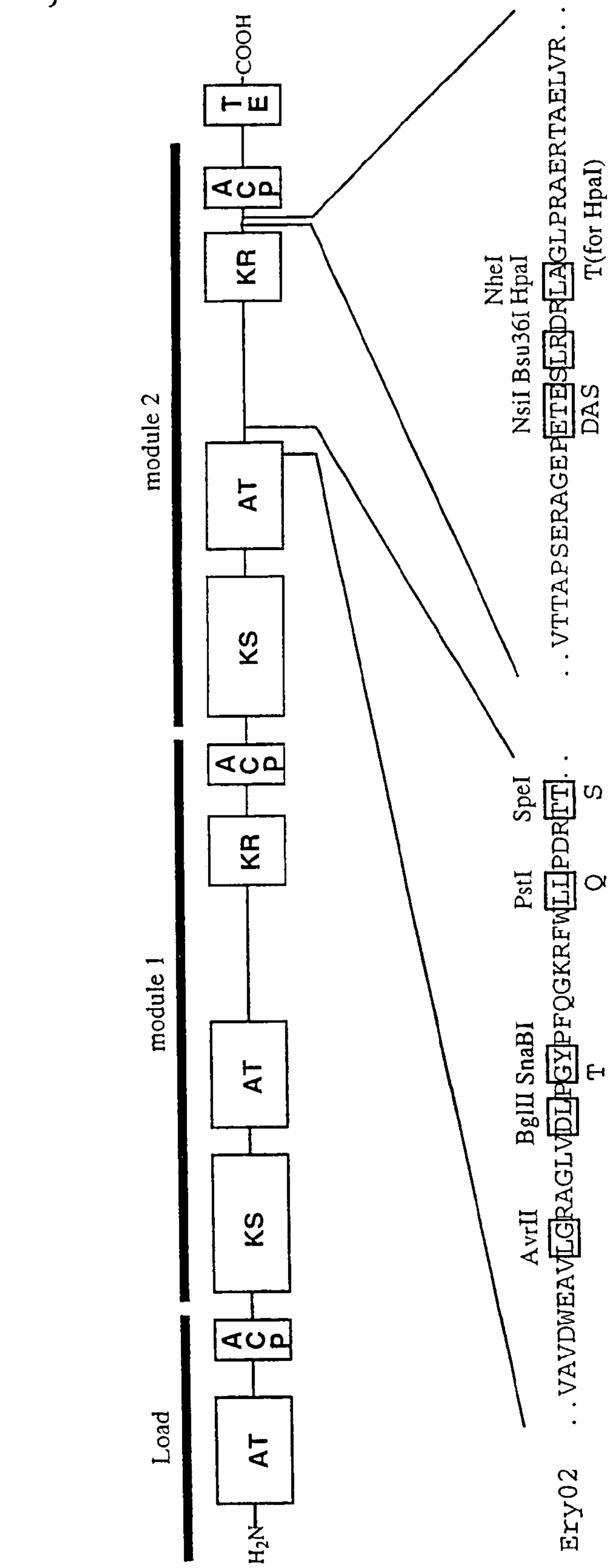
FIG. 2 shows the original amino acid sequence of DEBS module 2 (SEQ ID NOs: 36 and 37) and changes to this amino acid sequence resulting from the introduction of restriction sites for SnaBI, PstI, SpeI, NsiI and NheI.

These new restriction sites are situated partly in DNA encoding a linker region near positions where the polyketide synthase is hydrolysed by proteolytic enzymes (vide supra). While some of the restriction sites lie in DNA encoding regions of low homology, others are situated in DNA encoding highly conserved regions (FIG. 1 showing SEQ ID NOs: 36, 38, 40, 42, 44, 46, 48, 50, 52, and 54 in the left column from top to bottom and SEQ ID NOs: 37, 39, 41, 43, 45, 47, 49, 51, 53, and 55 in the right column from top to bottom). The introduction of recognition sites for the enzymes AvrII, BglII, Bsu36I and NheI does not change the amino acid sequence in DEBS module 2. In the other five cases (SnaBI, PstI, SpeI, Nsi, HpaI) the amino acid sequence is changed (FIG. 2 showing SEQ ID NOs: 36 (left) and 37 (right) and the changes for SnaBI; PstI SpeI; Nsi; and NheI). These changes do not affect the activity of the protein (see example 6).

Because two of the restriction sites cover the same bases it was decided to construct two plasmids containing different mcs (pJLK114 and pJLK117).

The use of an mcs offers the following advantages over a single restriction site on each side of the reductive loop:

1) suitable positions to join the DNA fragments (20 different combinations) can be chosen for every different reductive loop thereby avoiding unfavourable changes in the amino acid sequence
2) enzymes that cut within the loop can be avoided; and
3) loop insertion may be performed in a combinatorial way.

The present inventors have made the further surprising discovery that different results may be obtained using the same polylinker-containing nucleic acid and the same nucleic acid encoding one or more reductive enzymes, when the nucleic acid encoding one or more reductive enzymes is incorporated at different sites in the polylinker.

For example, in Examples 7 and 8, the reductive loop of the rapamycin module 13 was inserted into ery module 2 to bring about complete reduction of the polyketide chain as the outcome of the second extension module. The desired triketide lactone products were obtained in good yield. However, in Examples 37 and 38, the same reductive loop, or set of domains, from rap module 13 was inserted into essentially the same position in ery module 2 as in examples 7 and 8, save that different restriction sites of the polylinker were used (AvrII and HpaI instead of BglII and NsiI) and significant amounts of by-products were obtained. Such by-products included triketide lactones in which C-3 was either keto or hydroxy, showing that simply altering the sites used for swapping the reductive loop made the difference between obtaining the desired product and obtaining an undesirable mixture of the desired product with the products of incomplete reduction.

Similarly, in Examples 31 and 32, when the sites PstI and Bsu36I were used to insert the reductive domains of avermectin module 1 (plasmid pGMS2) in place of the reductive loop of ery module 2, the expected product was produced, but also a substantial amount of ketolactone. In the experiment of Examples 29 and 30, when the sites BglII and NheI were used (plasmid pJLK30) hardly any ketolactone byproduct was produced, although the amounts of lactone were in a similar range in each case.

When, entirely analogously to the Examples 29 and 30, in Example 14 the same sites BglII and NheI were used to replace the reductive loop of ery module 2 with the reductive loop of tylosin module 1 (plasmid pJLK35), the same target triketide lactones were produced as in Examples 30 and 32 but with much higher yield, albeit accompanied by some ketolactone, demonstrating that different reductive loops may be most advantageously inserted into different restriction sites.

In Examples 33 and 34, when the sites BglII and NheI were used to insert the reductive domains of avermectin module 2 (plasmid pJLK31) the expected products were produced as the major products. In the experiment of Examples 35 and 36, when the sites SnaBI and Bsu36I were used (plasmid pGMS4) only trace amounts of a triketide lactone mixture could be obtained.

Thus, the present invention provides the opportunity, should the desired and predicted products not be obtained when a particular reductive loop is inserted into a particular PKS, of simple adjustment of the insertion site by use of different restriction enzymes having sites in the polylinker. As demonstrated by the above comparative examples, such readjustment can dramatically affect the outcome and yield of polyketide synthesis.

Example 1

Construction of Plasmid pJLK114

Figure 3:
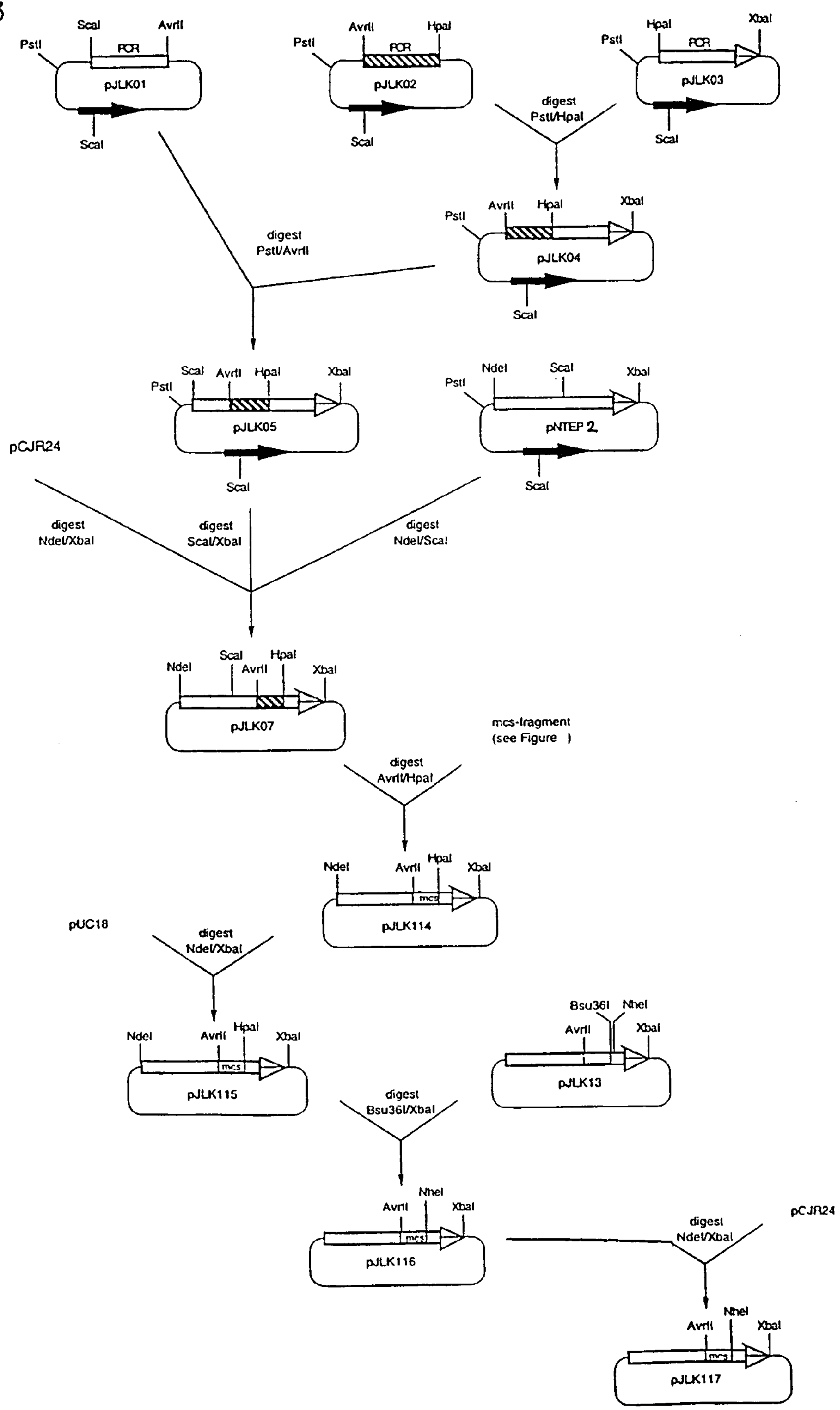
FIG. 3 is a flow chart depicting the construction of plasmids pJLK114 and pJLK117.

Plasmid pJLK114 is a pCJR24 based plasmid containing a PKS gene comprising the ery loading module, the first and the second extension modules of the ery PKS and the ery chain-terminating thioesterase except that the DNA segment between the end of the acyltransferase and the beginning of the ACP of the second ery extension module has been substituted by a synthetic oligonucleotide linker containing the recognition sites of the following restriction enzymes: AvrII, BglII, SnaBI, PstI, SpeI, NsiI, Bsu36I and HpaI. It was constructed via several intermediate plasmids as follows (FIG. 3).

Construction of Plasmid pJLK02

The approximately 1.47 kbp DNA fragment of the eryAI gene of *S. erythraea* was amplified by PCR using as primers the synthetic oligonucleotides: 5'-TACCTAGGCCGGGCCGGACTGGTCGACCTGCCGGGTT-3' (SEQ ID NO:2) and 5'-ATGTTAACCGGTCGCGCAGGCTCTCCGTCT-3' (SEQ ID NO: 3) and plasmid pNTEP2 (Oliynyk, M. et al., Chemistry and Biology (1996) 3: 833–839; WO98/01546) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK02 was identified by its restriction pattern and DNA sequencing.

Construction of Plasmid pJLK03

The approximately 1.12 kbp DNA fragment of the eryAI gene of *S. erythraea* was amplified by PCR using as primers the synthetic oligonucleotides: 5'-ATGTTAACGGGTCTGCCGCGTGCCGAGCGGAC-3' (SEQ ID NO: 4) and 5'-CTTCTAGACTATGAATTCCCTCCGCCCAGC-3' (SEQ ID NO: 5 and plasmid pNTEPH as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK03 was identified by its restriction pattern and DNA sequencing.

Construction of Plasmid pJLK04

Plasmid pJLK02 was digested with PstI and HpaI and the 1.47 kbp insert was ligated with plasmid pJLK03 which had been digested with PstI and HpaI. The ligation mixture was used to transform electrocompetent *E. coli* DH10B cells and individual colonies were checked for their plasmid content. The desired plasmid pJLK04 was identified by its restriction pattern.

Construction of Plasmid pJLK05

Plasmid pJLK01 (PCT/GB97/01819) was digested with PstI and AvrII and the 460 bp insert was ligated with plasmid pJLK04 which had been digested with PstI and AvrII. The ligation mixture was used to transform electrocompetent *E. coli* DH10B cells and individual colonies were checked for their plasmid content. The desired plasmid pJLK05 was identified by its restriction pattern.

Construction of Plasmid pJLK07

Plasmid pJLK05 was digested with ScaI and XbaI and plasmid pNTEP2 was digested with NdeI and ScaI and these two fragments were ligated with plasmid pCJR24 which had been digested with NdeI and XbaI. The ligation mixture was used to transform electrocompetent *E. coli* DH10B cells and individual colonies were checked for their plasmid content. The desired plasmid pJLK07 was identified by its restriction pattern.

Construction of Plasmid pJLK114

The two synthetic oligonucleotides Plf and Plb (FIG. 4 showing oligonucleotides Plf (SEQ ID NO: 56) and Plb (SEQ ID NO: 57) and the oligonucleotides annealed (SEQ ID NOs: 58–61 from top to bottom)) were each dissolved in TE-buffer. 10 $\mu$L of each solution (0.5 nmol/$\mu$L) were mixed and heated for 2 minutes at 65C and then slowly cooled down to room temperature. Plasmid pJLK07 was digested with AvrII and HpaI and ligated with the annealed oligonucleotides. The ligation mixture was used to transform electrocompetent *E. coli* DH10B cells and individual colonies were checked for their plasmid content. The desired plasmid pJLK114 was identified by its restriction pattern.

Example 2

Use of Plasmid pJLK114 for Construction of *S. erythraea* JC2/pJLK114 and the Production of TKL Derivatives Approximately 5 $\mu$g plasmid pJLK114 were used to transform protoplasts of *S. erythraea* JC2 (strain deposited as No. NCIMB 40802. WO98/01546.) and stable thiostrepton resistant colonies were isolated. From several colonies total DNA was obtained and analysed by Southern blot hybridisation, to confirm that the plasmid has integrated into the TE gene. JC2/pJLK114 was plated onto SM3 agar (5.0 g glucose, 50.0 g MD30E maltodextrin, 25.0 g Arkasoy soya flour, 3.0 g molasses (beet), 0.25 g $K_2HPO_4$, 2.5 g $CaCO_3$ 22.0 g agar distilled water to 1 liter pH=7.0) containing 50 $\mu$g/ml thiostrepton and allowed to grow for twelve days at 30° C. 1 $cm^2$ (500 $\mu$l) of the plate was homogenised and extracted with a mixture of 1.2 ml ethyl acetate and 20 ul formic acid. The solvent was decanted and removed by evaporation and the residue dissolved in methanol and analysed by GC/MS and electrospray mass spectroscopy. The major products were identified as (4S, 5R)-5-hydroxy-2,4-dimethyl-3-oxo-n-hexanoic acid-δ-lactone and as (4S, 5R)-5-hydroxy-2,4-dimethyl-3-oxo-n-heptanoic acid-δ-lactone.

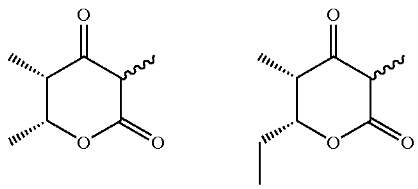

Example 3

Construction of Plasmid pJLK117

Plasmid PJLK117 is a pCJR24 based plasmid containing a PKS gene comprising the ery loading module, the first and the second extension modules of the ery PKS and the ery chain-terminating thioesterase except that the DNA segment between the end of the acyltransferase and the beginning of the ACP of the second ery extension module has been substituted by a synthetic oligonucleotide linker containing the recognition sites of the following restriction enzymes. AvrII, BglII, SnaBI, PstI, SpeI, NsiI, Bsu36I and NheI.

It was constructed via several intermediate plasmids as follows (FIG. 3).

Construction of Plasmid pJLK115

Plasmid pJLK114 was digested with NdeI and XbaI and the approximately 9.9 kbp insert was ligated with plasmid pUC18 which had been digested with NdeI and XbaI. The ligation mixture was used to transform electrocompetent *E. coli* DH10B cells and individual colonies were checked for their plasmid content. The desired plasmid pJLK115 was identified by its restriction pattern.

Construction of Plasmid pJLK116

Plasmid pJLK13 (PCT/GB97/01819) was digested with Bsu36I and XbaI and the 1.1 kbp fragment was ligated with plasmid pJLK115 which had been digested with Bsu36I and XbaI. The ligation mixture was used to transform electrocompetent *E. coli* DH10B cells and individual colonies were checked for their plasmid content. The desired plasmid pJLK116 was identified by its restriction pattern.

Construction of Plasmid pJLK117

Plasmid pJLK116 was digested with NdeI and XbaI and the 9.9 kbp fragment was ligated with plasmid pCJR24 which had been digested with NdeI and XbaI. The ligation mixture was used to transform electrocompetent *E. coli* DH10B cells and individual colonies were checked for their plasmid content. The desired plasmid pJLK117 was identified by its restriction pattern.

Example 4

Use of Plasmid pJLK117 for Construction of *S. erythraea* JC2/pJLK117 and the Production of TKL Derivatives Approximately 5 μg plasmid pJLK117 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pJLK117 was plated onto SM3 agar containing 50 μg/ml thiostrepton and allowed to grow for twelve days at 30° C. 1 $cm^2$ (0.5 ml) of the plate was homogenised and extracted with a mixture of 1.2 ml ethyl acetate and 20 ul formic acid. The solvent was decanted and removed by evaporation and the residue dissolved in methanol and analysed by GC/MS and electrospray mass spectroscopy. The major products were identified as (4S, 5R)-5-hydroxy-2,4-dimethyl-3-oxo-n-hexanoic acid-δ-lactone and as (4S, 5R)-5-hydroxy-2,4-dimethyl-3-oxo-n-heptanoic acid-δ-lactone.

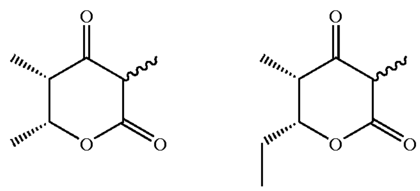

Example 5

Construction of Plasmid pJLK25

Plasmid pJLK25 is a PJLK114 based plasmid except that the DNA fragment encoding the reductive loop of the second module of the erythromycin PKS gene has been inserted into the mcs.

It was constructed via several intermediate plasmids as follows.

Construction of Plasmid pJLK118

The approximately 1.4 kbp DNA fragment of the eryAI gene of *S. erythraea* encoding the reductive loop of module 2 was amplified by PCR using as primers the synthetic oligonucleotides: 5'-ATACTAGTCCTCGTGACGAGCTCGACGG-3' (SEQ ID NO: 6) and 5'-TAATGCATCCGGTTCTCCGGCCCGCTCGCT-3' (SEQ ID NO: 7) and pNTEP2 as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK118 was identified by its restriction pattern and DNA sequencing.

Construction of Plasmid pJLK23

Plasmid pJLK118 was digested with SpeI and NsiI and the 1.4 kbp fragment was ligated with plasmid pJLK115 which had been digested with SpeI and NsiI. The ligation mixture was used to transform electrocompetent *E. coli* DH10B cells and individual colonies were checked for their plasmid content. The desired plasmid pJLK23 was identified by its restriction pattern.

Construction of Plasmid pJLK25

Plasmid pJLK23 was digested with NdeI and XbaI and the approximately 11.2 kbp fragment was ligated with plasmid pCJR24 which had been digested with NdeI and XbaI. The ligation mixture was used to transform electrocompetent *E. coli* DH10B cells and individual colonies were checked for their plasmid content. The desired plasmid pJLK25 was identified by its restriction pattern.

Example 6

Use of Plasmid pJLK25 for Construction of *S. erythraea* JC2/pJLK25 and the Production of Triketides Approximately 5 μg plasmid pJLK25 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pJLK25 was plated onto SM3 agar containing 50 μg/ml thiostrepton and allowed to grow for twelve days at 30° C. 1 $cm^2$ (0.5 ml) of the plate was homogenised and extracted with a mixture of 1.2 ml ethyl acetate and 20 ul formic acid. The solvent was decanted and removed by evaporation and the residue dissolved in methanol and analysed by GC/MS and electrospray mass spectroscopy. The major products were identified (by comparison with authentic material) as (2R, 3S, 4S, 5R)-5,3-dihydroxy-2,4-dimethyl-n-hexanoic acid δ-lactone and as (2R, 3S, 4S, 5R)-5,3-dihydroxy-2,4-dimethyl-n-heptanoic acid δ-lactone.

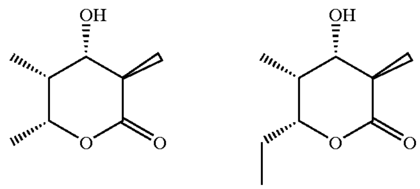

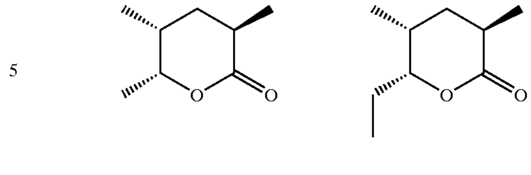

Example 9

Example 7

Construction of Plasmid pJLK28

Figure 5A:
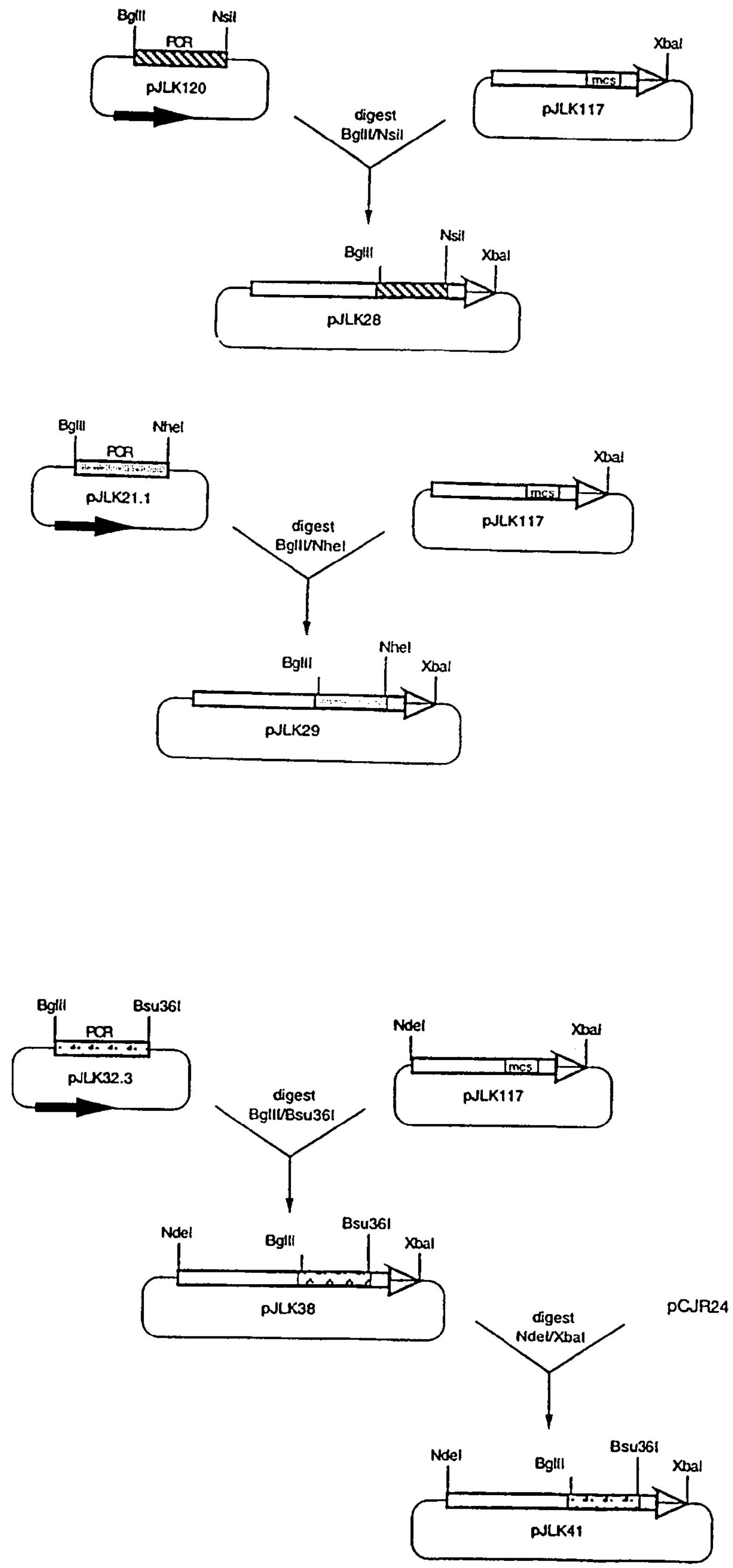
FIG. 5*a* is a flow chart depicting the construction of pJLK28, pJLK29 and pJLK41.

Plasmid pJLK28 is a pJLK117 based plasmid except that the DNA fragment encoding the reductive loop of module 13 of the rap PKS has been inserted into the mcs. It was constructed via several intermediate plasmids as follows. (FIG. 5)

Construction of Plasmid pJLK120

The approximately 3.2 kbp DNA segment of the rapC gene of *S. hygroscopicus* encoding the reductive loop of module 13 was amplified by PCR using as primers the synthetic oligonucleotides: 5'-TAAGATCTTCCGACCTACGCCTTCCAAC-3' (SEQ ID NO: 8) and 5'-TAATGCATCGACCTCGTTGCGTGCCGCGGT-3' (SEQ ID NO: 9) and cosmid cos 31 (Schwecke, T. et al. (1995) Proc. Natl. Acad. Sci. USA 92: 7839–7843) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK120 was identified by its restriction pattern and DNA sequencing.

Construction of Plasmid pJLK28

Plasmid pJLK120 was digested with BglII and NsiI and the 3.2 kbp fragment was ligated with plasmid pJLK117 which had been digested with BglII and NsiI. The ligation mixture was used to transform electrocompetent *E. coli* DH10B cells and individual colonies were checked for their plasmid content. The desired plasmid pJLK28 was identified by its restriction pattern.

Example 8

Use of Plasmid pJLK28 for Construction of JC2/pJLK28 and the Production of Triketides Approximately 5 μg plasmid pJLK28 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pJLK28 was plated onto SM3 agar containing 50 μg/ml thiostrepton and allowed to grow for twelve days at 30° C. 1 $cm^2$ (0.5 ml) of the plate was homogenised and extracted with a mixture of 1.2 ml ethyl acetate and 20 ul formic acid. The solvent was decanted and removed by evaporation and the residue dissolved in methanol and analysed by GC/MS and electrospray mass spectroscopy. The major products were identified (by comparison with authentic material) as (2R, 4S, 5R)-2,4-dimethyl-5-hydroxy-n-hexanoic acid δ-lactone and as (2R, 4S, 5R)-2,4-dimethyl-5-hydroxy-n-heptanoic acid δ-lactone.

Construction of Plasmid pJLK41

Plasmid pJLK41 is a pJLK117 based plasmid except that the DNA fragment encoding the reductive loop of module 4 of the ery PKS has been inserted into the mcs. It was constructed via several intermediate plasmids as follows. (FIG. 5)

Construction of Plasmid pJLK32.3

The approximately 3.2 kbp DNA segment of the eryAII gene of *S. erythraea* encoding the reductive loop of module 4 was amplified by PCR using as primers the synthetic oligonucleotides: 5'-ATAGATCTGCCTACGTACCCGTTCGAACACCAGCGCTTC-3' (SEQ ID NO: 10) and 5'-ATCCTCAGGTTCGGCCCTGCCGCCTCGGCCTGCCCGGCGGCGCGCAGCTT-3' (SEQ ID NO: 11) and cosmid cos4B (cosmid containing the erythromycin PKS) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK32.3 was identified by its restriction pattern and DNA sequencing.

Construction of Plasmid pJLK38

Plasmid pJLK32.3 was digested with BglII and Bsu36I and the 3.2 kbp fragment was ligated with plasmid pJLK116 which had been digested with BglII and Bsu36I. The ligation mixture was used to transform electrocompetent *E. coli* DH10B cells and individual colonies were checked for their plasmid content. The desired plasmid pJLK38 was identified by its restriction pattern.

Construction of Plasmid pJLK41

Plasmid pJLK38 was digested with NdeI and XbaI and the approximately 13 kbp fragment was ligated with plasmid pCJR24 which had been digested with NdeI and XbaI. The ligation mixture was used to transform electrocompetent *E. coli* DH10B cells and individual colonies were checked for their plasmid content. The desired plasmid pJLK41 was identified by its restriction pattern.

Example 10

Use of Plasmid pJLK41 for Construction of JC2/pJLK41 and the Production of Triketides Approximately 5 μg plasmid pJLK41 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pJLK41 was plated onto SM3 agar containing 50 μg/ml thiostrepton and allowed to grow for twelve days at 30° C. 1 $cm^2$ (0.5 ml) of the plate was homogenised and extracted with a mixture of 1.2 ml ethyl acetate and 20 ul formic acid.

The solvent was decanted and removed by evaporation and the residue dissolved in methanol and analysed by GC/MS and electrospray mass spectroscopy. The major products were identified (by comparison with authentic material) as (2S, 4S, 5R)-2,4-dimethyl-5-hydroxy-n-hexanoic acid δ-lactone and as (2S, 4S, 5R)-2,4-dimethyl-5-hydroxy-n-heptanoic acid δ-lactone.

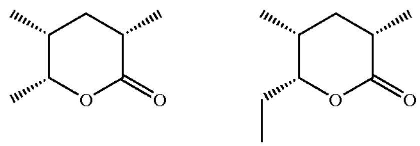

Example 11

Construction of Plasmid pJLK29

Plasmid pJLK29 is a pJLK117 based plasmid except that the DNA fragment encoding the reductive loop of module 10 of the rap PKS has been inserted into the mcs. It was constructed via several intermediate plasmids as follows. (FIG. 5)

Construction of Plasmid pJLK121.1

The approximately 2.2 kbp DNA segment of the rapB gene of *S. hygroscopicus* encoding the reductive loop of module 10 was amplified by PCR using as primers the synthetic oligonucleotides: 5'-TAAGATCTTCCGACGTACGCGTTCCAGC-3' (SEQ ID NO: 12) and 5'-ATGCTAGCCACTGCGCCGACGAATCACCGGTGG-3' (SEQ ID NO: 13) and as template an approximately 7 kbp fragment, which has been obtained by digestion of cosmid cos 26 (Schwecke, T. et al. (1995) Proc. Natl. Acad. Sci. USA 92: 7839–7843) with ScaI and SphI. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK121.1 was identified by its restriction pattern and DNA sequencing.

Construction of Plasmid pJLK29

Plasmid pJLK121.1 was digested with BglII and NheI and the 2.2 kbp fragment was ligated with plasmid pJLK117 which had been digested with BglII and NheI. The ligation mixture was used to transform electrocompetent *E. coli* DH10B cells and individual colonies were checked for their plasmid content. The desired plasmid pJLK29 was identified by its restriction pattern.

Example 12

Use of Plasmid pJLK29 for Construction of *S. erythraea* JC2/pJLK29 and the Production of Triketides Approximately 5 μg plasmid pJLK29 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pJLK29 was used to inoculate 30 ml of SM3 medium containing 5 μg/ml thiostrepton in a 250 ml flask with a single spring to reduce clumping, shaken at 300 rpm and at 30° C. After 8 days the broth was centrifuged, the supernatant adjusted to pH 3 and extracted three times with an equal volume of ethyl acetate. The solvent was removed by evaporation and the residue dissolved in methanol and analysed by HPLC and electrospray mass spectroscopy and, after conversion to the methyl ester with trimethylsilyldiazomethane by GC/MS. The major products were identified (by comparison with authentic material) as (4S, 5R)-5-hydroxy-2,4-dimethyl-n-hex-2-enoic acid and as (4S, 5R)-5-hydroxy-2,4-dimethyl0-n-hept-2-enoic acid.

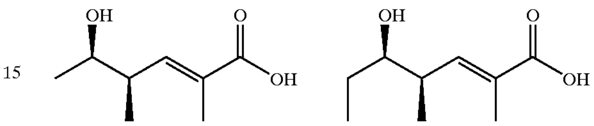

Example 13

Construction of Plasmid pJLK35

Plasmid pJLK35 is a pJLK117 based plasmid except that the DNA fragment encoding the reductive loop of module 1 of the tylosin PKS has been inserted into the mcs. It was constructed via several intermediate plasmids as follows. (FIG. 5)

Construction of Plasmid pJLK33.1

The approximately 1.6 kbp DNA segment of the tylosin PKS gene of *S. fradiae* encoding the reductive loop of module 1 was amplified by PCR using as primers the synthetic oligonucleotides: 5'-TAAGATCTCCCTACGTACCCCTTCAACCAC-3' (SEQ ID NO: 14) and 5'-GCTAGCCGCCGCGCCAGCTCGGGC-3' (SEQ ID NO: 15) and cosmid 6T (cosmid containing the tylosin-producing PKS genes) as template The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK33.1 was identified by its restriction pattern and DNA sequencing.

Construction of Plasmid pJLK35

Plasmid pJLK33.1 was digested with BglII and NheI and the 1.6 kbp fragment was ligated with plasmid pJLK117 which had been digested with BglII and NheI. The ligation mixture was used to transform electrocompetent *E. coli* DH10B cells and individual colonies were checked for their plasmid content. The desired plasmid pJLK35 was identified by its restriction pattern.

Example 14

Use of Plasmid pJLK35 for Construction of *S. erythraea* JC2/pJLK35 and the Production of Triketides Approximately 5 μg plasmid pJLK35 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pJLK35 was plated onto SM3 agar containing 50 μg/ml thiostrepton and allowed to grow for twelve days at 30° C. 1 $cm^2$ (0.5 ml) of the plate was homogenised and extracted with a mixture of 1.2 ml ethyl acetate and 20 ul formic acid.

The solvent was decanted and removed by evaporation and the residue dissolved in methanol and analysed by GC/MS and electrospray mass spectroscopy. The major products were identified (by comparison with authentic material) as (2R, 3R, 4S, 5R)-5,3-dihydroxy-2,4-dimethyl-n-hexanoic acid δ-lactone and as (2R, 3R, 4S, 5R)-5,3-dihydroxy-2,4-dimethyl-n-heptanoic acid δ-lactone.

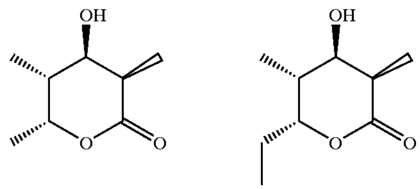

Example 15

Construction of Plasmid pRIF7

Plasmid pRIF7 is a pJLK117 based plasmid except that the DNA fragment encoding the reductive loop of module 7 of the rifamycin PKS has been inserted into the mcs. It was constructed via several intermediate plasmids as follows. (FIG. 5)

Construction of Plasmid pUCRIF7

The approximately 2.1 kbp DNA segment of the rifamycin PKS gene of Amycolatopsis mediterranei encoding the reductive loop of module 7 was amplified by PCR using as primers the synthetic oligonucleotides: 5'-CCTACGTACGCCTTCGACCACCAGCACTT-3' (SEQ ID NO: 16) and 5'-CGGCTAGCGGGCGTTCCAGGCCGCCGTCCT (SEQ ID NO: 17) and cosmid 6 (cosmid starting at 35727 and going beyond 76199, numbers according to accession number AF040570) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pUCRIF7 was identified by its restriction pattern and DNA sequencing.

Construction of Plasmid pRIF7

Plasmid pUCRIF7 was digested with SnaBI and NheI and the 2.1 kbp fragment was ligated with plasmid pJLK117 which had been digested with SnaBI and NheI. The ligation mixture was used to transform electrocompetent *E. coli* DH10B cells and individual colonies were checked for their plasmid content. The desired plasmid pRIF7 was identified by its restriction pattern.

Example 16

Use of Plasmid pRIF7 for Construction of *S. erythraea* JC2/pRIF7 and the Production of Triketides Approximately 5 μg plasmid pRIF7 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pRIF7 was plated onto SM3 agar containing 50 μg/ml thiostrepton and allowed to grow for twelve days at 30° C. 1 $cm^2$ of the plate was homogenised and extracted with a mixture of 1.2 ml ethyl acetate and 20 ul formic acid. The solvent was decanted and removed by evaporation and the residue dissolved in methanol and analysed by GC/MS and electrospray mass spectroscopy. The major products were identified (by comparison with authentic material) as (2S, 3S, 4S, 5R)-5,3-dihydroxy-2,4-dimethyl-n-hexanoic acid δ-lactone and as (2R, 3R, 4S, 5R)-5,3-dihydroxy-2,4-dimethyl-n-heptanoic acid δ-lactone.

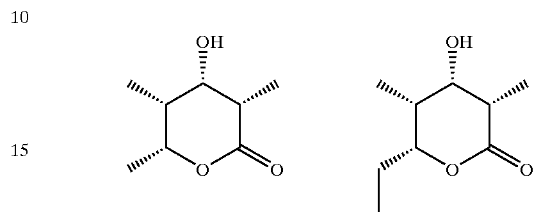

Example 17

Construction of Plasmid pJLK52

Plasmid pJLK52 is a pJLK35 based plasmid containing a PKS gene comprising the ery loading module, the first, the second and the third extension modules of the ery cluster and the ery chain-terminating thioesterase except that the DNA segment between the end of the acyltransferase and the beginning of the ACP of the second ery extension module has been substituted by the equivalent segment of module 1 of the tylosin PKS.

It was constructed via several intermediate plasmids as follows.

Construction of Plasmid pJLK50

The approximately 6.1 kbp DNA segment of the erythromycin PKS gene cluster of *S. erythraea* encoding the DNA fragment from the beginning of the ACP of module 2 to the beginning of the ACP of module 3 was amplified by PCR using as primers the synthetic oligonucleotides: 5'-TACCTGAGGGACCGGCTAGCGGGTCTGCCGCGTG-3' (SEQ ID NO: 18) and 5'-ATGCTAGCCGTTGTGCCGGCTCGCCGGTCGGTCC-3' (SEQ ID NO: 19) and plasmid pBAM25 as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK50 was identified by its restriction pattern and DNA sequencing.

Construction of Plasmid pJLK52

Plasmid pJLK50 was digested with NheI and the 6.1 kbp insert was ligated with plasmid pJLK35 which had been digested with NheI. The ligation mixture was used to transform electrocompetent *E. coli* DH10B cells and individual colonies were checked for their plasmid content. The desired plasmid pJLK52 was identified by its restriction pattern.

Example 18

Use of Plasmid pJLK52 for Construction of *S. erythraea* NRRL2338/pJLK52 and the Production of Tetraketides and Macrolides Approximately 5 μg plasmid pJLK52 were used to transform protoplasts of *S. erythraea* NRRL2338 and stable thiostrepton resistant colonies were isolated. From several colonies total DNA is obtained and analysed by Southern blot hybridisation, to confirm that the plasmid has integrated into the TE.

*S. erythraea* NRRL2338/pJLK52 was used to inoculate SM3 medium containing 5 μg/ml thiostrepton and allowed to grow for seven to twelve days at 28–30° C. After this time the broth was centrifuged and the pH of the supernatant adjusted to pH=9.5. The supernatant was then extracted three times with an equal volume of ethyl acetate and the solvent was removed by evaporation. The residue was dissolved in methanol and analysed by GC/MS by HPLC/MS and MS-MS. Tetraketides were identified by GC/MS. The major components were

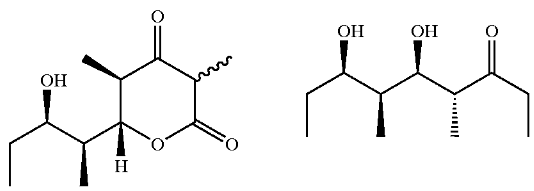

The following macrolide was identified by HPLC/MS, MS-MS and $^1$H-NMR (it was accompanied by products of incomplete processing by post-PKS enzymes)

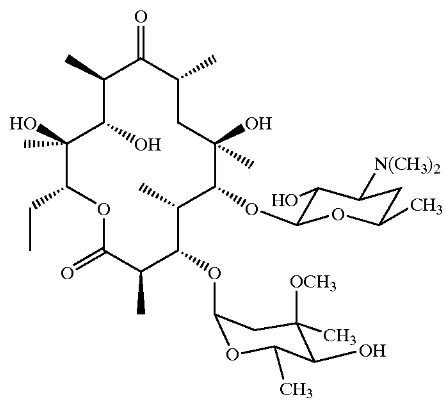

Example 19

Construction of Plasmid pJLK53

Plasmid pJLK53 is a pJLK28 based plasmid containing a PKS gene comprising the ery loading module, the first, the second and the third extension modules of the ery cluster and the ery chain-terminating thioesterase except that the DNA segment between the end of the acyltransferase and the beginning of the ACP of the second ery extension module has been substituted by the equivalent segment of module 13 of the rapamycin PKS. It was constructed as follows.

Plasmid pJLK50 was digested with NheI and the 6.1 kbp insert was ligated with plasmid pJLK28 which had been digested with NheI. The ligation mixture was used to transform electrocompetent *E. coli* DH10B cells and individual colonies were checked for their plasmid content. The desired plasmid pJLK53 was identified by its restriction pattern.

Example 20

Use of Plasmid pJLK53 for Construction of *S. erythraea* NRRL2338/pJLK53 and the Production of TKL Derivatives Approximately 5 μg plasmid pJLK53 were used to transform protoplasts of *S. erythraea* NRRL2338 and stable thiostrepton resistant colonies were isolated. From several colonies total DNA is obtained and analysed by Southern blot hybridisation, to confirm that the plasmid has integrated into the TE.

*S. erythraea* NRRL2338/pJLK53 was used to inoculate SM3 medium containing 5 μg/ml thiostrepton and allowed to grow for seven to ten days at 28–30° C. After this time the broth was centrifuged and the pH of the supernatant adjusted to pH=9.5. The supernatant was then extracted three times with an equal volume of ethyl acetate and the solvent was removed by evaporation. The residue was dissolved in methanol and analysed by GC/MS by HPLC/MS and MS-MS. Tetraketides were identified by GC/MS. The major component was

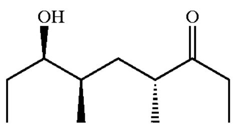

The following macrolide was identified by HPLC/MS, MS-MS and $^1$H-NMR (it was accompanied by products of incomplete processing by post-PKS enzymes)

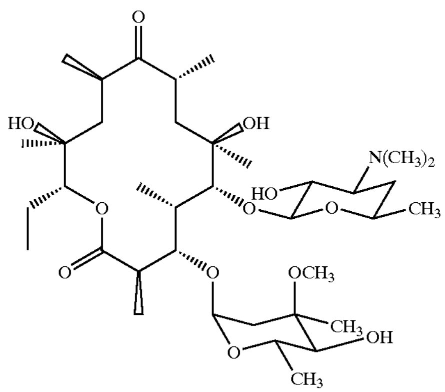

Example 21

Construction of Plasmid pJLK54

Plasmid pJLK54 is a pJLK29 based plasmid containing a PKS gene comprising the ery loading module, the first, the second and the third extension modules of the ery cluster and the ery chain-terminating thioesterase except that the DNA segment between the end of the acyltransferase and the beginning of the ACP of the second ery extension module has been substituted by the equivalent segment of module 10 of the rapamycin PKS.

It was constructed as follows.

Plasmid pJLK50 was digested with NheI and the 6.1 kbp insert was ligated with plasmid pJLK29 which had been digested with NheI. The ligation mixture was used to transform electrocompetent *E. coli* DH10B cells and individual colonies were checked for their plasmid content. The desired plasmid pJLK54 was identified by its restriction pattern.

Example 22

Use of Plasmid pJLK54 for Construction of *S. erythraea* NRRL2338/pJLK54 and the Production of Tetraketide Derivatives and Macrolides Approximately 5 μg plasmid pJLK54 were used to transform protoplasts of *S. erythraea* NRRL2338 and stable thiostrepton resistant colonies were isolated. From several colonies total DNA is obtained and analysed by Southern blot hybridisation, to confirm that the plasmid has integrated into the TE.

*S. erythraea* NRRL2338/pJLK54 was used to inoculate SM3 medium containing 5 μg/ml thiostrepton and allowed to grow for seven to ten days at 28–30° C. After this time the broth was centrifuged and the pH of the supernatant adjusted to pH=9.5. The supernatant was then extracted three times with an equal volume of ethyl acetate and the solvent was removed by evaporation. The residue was dissolved in methanol and analysed by GC/MS by HPLC/MS and MS-MS. Tetraketides were identified by GC/MS. The major component was

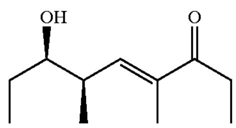

The following macrolide was identified by HPLC/MS, MS-MS and $^1$H-NMR (it was accompanied by products of incomplete processing by post-PKS enzymes).

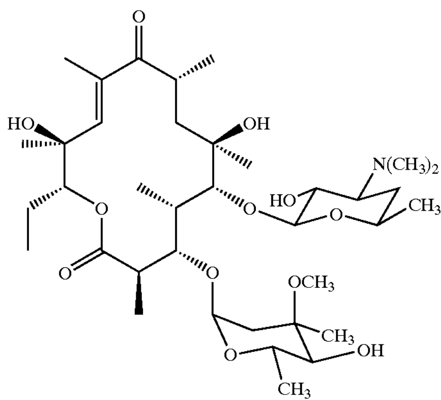

Avermectins

Example 23

Construction of pJLK136

Figure 6:
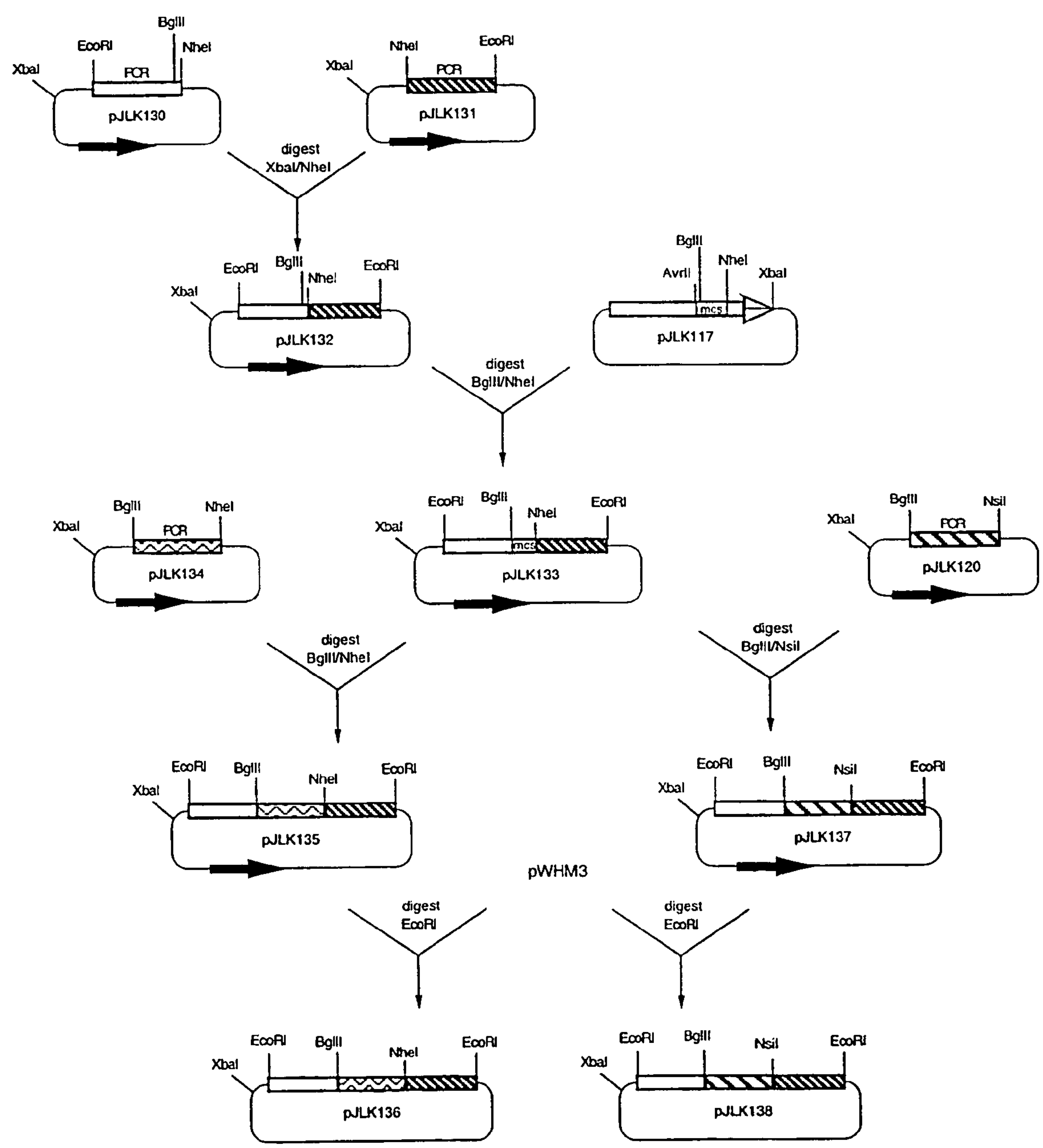
FIG. 6 is a flow chart depicting the construction of pJLK136.

Plasmid pJLK136 is a pWHM3 based plasmid comprising the upstream and the downstream flanking region of the reductive loop of module 2 of the avermectin PKS gene and the erythromycin resistance gene inserted into the mcs which connects these two fragments. Plasmid pWHM3 is described in Vara J et al, J Bacteriol 1989, 171: 5872–5881. Plasmid pJLK136 was constructed via several intermediate plasmids as follows (FIG. 6).

Construction of pJLK130

The approximately 2.4 kbp DNA segment of the avermectin PKS gene of *S. avermitilis* encoding the region upstream of the reductive loop of module 2 was amplified by PCR using as primers the synthetic oligonucleotides: 5'-GACGCCGAATTCTTCGGCATCAGC-CCCCGCGAAG-3' (SEQ ID NO: 20) and 5'-GAGCTAG-CAGGTGGGGAGATCTAGGTGGGT-GTGGGTGTGGGGTTGGTTGTGGTGGTGG GTGTA-3' (SEQ ID NO: 21) and plasmid pIG22 (Galloway, I. S. (1998) Thesis, University of Cambridge, UK) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK130 was identified by its restriction pattern and DNA sequencing.

Construction of pJLK131

The approximately 2.0 kbp DNA segment of the avermectin PKS gene of *S. avermitilis* encoding the region downstream of the reductive loop of module 2 was amplified by PCR using as primers the synthetic oligonucleotides: 5'-GCCCGGCTAGCCGGCCAGACACACGAA-CAACAGC-3' (SEQ ID NO: 22) and 5'-GGGAATTCCTC-GAGGATGACGTGGGCGTTGGTGC-3' (SEQ ID NO: 23) and plasmid pIG25 (Galloway, I. S. (1998) Thesis, University of Cambridge, UK) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK131 was identified by its restriction pattern and DNA sequencing.

Construction of Plasmid pJLK132

Plasmid pJLK130 was digested with NheI and XbaI and the approximately 2.4 kbp insert was ligated with plasmid pJLK131 which had been digested with NheI and XbaI. The ligation mixture was used to transform electrocompetent E. coli DH10B cells and individual colonies were checked for their plasmid content. The desired plasmid pJLK132 was identified by its restriction pattern.

Construction of Plasmid pJLK133

Plasmid pJLK117 was digested with BglII and NheI and the approximately 0.1 kbp insert was ligated with plasmid pJLK132 which had been digested with BglII and NheI. The ligation mixture was used to transform electrocompetent *E. coli* DH10B cells and individual colonies were checked for their plasmid content. The desired plasmid pJLK132 was identified by its restriction pattern.

Construction of pJLK134

The approximately 1.9 kbp DNA segment of the erythromycin gene cluster of *S. erythraea* encoding the erythromycin resistance was amplified by PCR using as primers the synthetic oligonucleotides: 5'-TAAGATCTAGCGCTC-CGAGGTTCTTGCCCG-3' (SEQ ID NO: 24) and 5'-AT-GCTAGCCTACCGCTGCCCGGGTCCGCCG-3' (SEQ IS NO: 25) and plasmid pRH3 (Dhillon, N, et al. Molecular Microbiology (1989) 3: 1405–1414) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK134 was identified by its restriction pattern and DNA sequencing.

Construction of Plasmid pJLK135

Plasmid pJLK134 was digested with BglII and NheI and the approximately 1.9 kbp insert was ligated with plasmid pJLK133 which had been digested with BglII and NheI. The ligation mixture was used to transform electrocompetent *E. coli* DH10B cells and individual colonies were checked for their plasmid content. The desired plasmid pJLK135 was identified by its restriction pattern.

Construction of Plasmid pJLK136

Plasmid pJLK135 was digested with EcoRI and the approximately 6.3 kbp insert was ligated with plasmid pWHM3 which had been digested with EcoRI and then treated with alkaline phosphatase. The ligation mixture was used to transform electrocompetent *E. coli* DH10B cells and individual colonies were checked for their plasmid content. The desired plasmid pJLK136 was identified by its restriction pattern.

Example 24

Use of Plasmid pJLK136

Approximately 10 μg plasmid pJLK136 were used to transform protoplasts of *S. avermitilis* (MacNeil, D. J. and Klapko, C. M. Journal of Industrial Microbiology (1987) 2:209–218) and stable thiostrepton and erythromycin resistant colonies were isolated. Individual colonies were selected and subcultured four times in non-selective liquid medium followed by preparation and regeneration of protoplasts (media according to MacNeil T. et al J. Bacteriol. (1993) 175:2552–2563) Thiostrepton sensitive and erythromycin resistant colonies were isolated and characterised by Southern blot hybridisation. One such colony was designated *S. avermitilis*/JLKl.

Example 25

Construction of Plasmid pJLK137

Plasmid pJLK120 was digested with BglII and NsiI and the approximately 3.2 kbp insert was ligated with plasmid pJLK133 which had been digested with BglII and NsiI. The ligation mixture was used to transform electrocompetent *E. coli* DH10B cells and individual colonies were checked for their plasmid content. The desired plasmid pJLK137 was identified by its restriction pattern.

Construction of Plasmid pJLK138

Plasmid pJLK137 was digested with EcoRI and the approximately 7.6 kbp insert was ligated with plasmid pWHM3 which had been digested with EcoRI and then treated with alkaline phosphatase. The ligation mixture was used to transform electrocompetent *E. coli* DH10B cells and individual colonies were checked for their plasmid content. The desired plasmid pJLK138 was identified by its restriction pattern.

Example 26

Use of Plasmid pJLK138

Approximately 10 μg plasmid pJLK138 were used to transform protoplasts of *S. avermitilis* (MacNeil, D. J. and Klapko, C. M. Journal of Industrial Microbiology (1987) 2:209–218) and stable thiostrepton and erythromycin resistant colonies were isolated. Individual colonies were selected subcultured four times in non-selective liquid medium followed by preparation and regeneration of protoplasts (media according to MacNeil T. et al J. Bacteriol. (1993) 175:2552–2563) Thiostrepton and erythromycin sensitive colonies were isolated and characterised by Southern blot hybridisation. One colony of *S. avermitilis*/pJLK138 was used to inoculate liquid media (fermentation according to Pang, C-H. et al J. of Antibiotics (1995) 48:59–66). the cultures were harvested and the products isolated and purified as described in the literature (Pang, C-H. et al J. of Antibiotics (1995) 48:59–66). The products were analysed by HPLC/MS and $^{1}$H-NMR and the following compound could be identified:

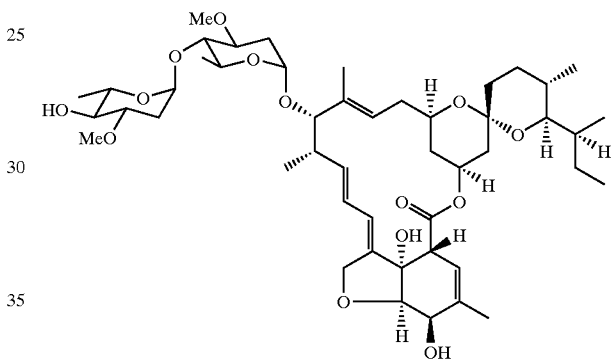

Example 27

Construction of Plasmid pJLK139

Plasmid pJLK121.1 was digested with BglII and NheI and the 2.2 kbp fragment was ligated with plasmid pJLK133 which had been digested with BglII and NheI. The ligation mixture was used to transform electrocompetent *E. coli* DH10B cells and individual colonies were checked for their plasmid content. The desired plasmid pJLK139 was identified by its restriction pattern.

Construction of Plasmid pJLK140

Plasmid pJLK139 was digested with EcoRI and the approximately 6.6 kbp insert was ligated with plasmid pWHM3 which had been digested with EcoRI and then treated with alkaline phosphatase. The ligation mixture was used to transform electrocompetent *E. coli* DH10B cells and individual colonies were checked for their plasmid content. The desired plasmid pJLK140 was identified by its restriction pattern.

Example 28

Use of Plasmid pJLK140

Approximately 10 μg plasmid pJLK140 were used to transform protoplasts of *S. avermitilis* (MacNeil, D. J. and Klapko, C. M. Journal of Industrial Microbiology (1987)

2:209–218) and stable thiostrepton and erythromycin resistant colonies were isolated. Individual colonies were selected and subcultured four times in non-selective liquid medium followed by preparation and regeneration of protoplasts (media according to MacNeil T. et al J. Bacteriol. (1993) 175:2552–2563) Thiostrepton and erythromycin sensitive colonies were isolated and characterised by Southern blot hybridisation. One colony of *S. avermitilis*/pJLK140 was used to inoculate liquid media (fermentation according to Pang, C-H. et al J. of Antibiotics (1995) 48:59–66). the cultures were harvested and the products isolated and purified as described in the literature (Pang, C-H. et al J. of Antibiotics (1995) 48:59–66). The products were analysed by HPLC/MS and 1H-NMR and the following compound could be identified:

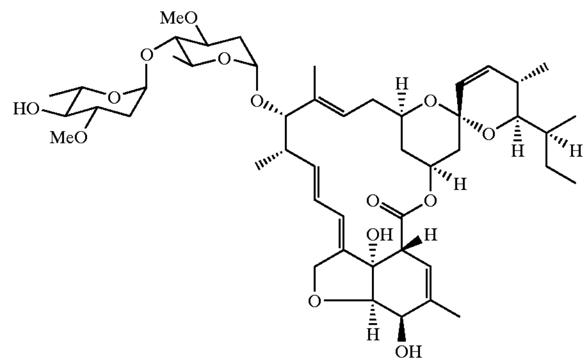

Example 29

Construction of Plasmid pJLK30 pJLK30 is a PJLK117 based plasmid except that the DNA encoding the reductive loop of module 1 of the avermectin PKS has been inserted into the polylinker using the restriction sites BglII and NheI. It was constructed via several intermediate plasmids.

Construction of Plasmid pIG67

The approximately 1.7 kbp DNA segment of the gene of the avermectin PKS of *S. avermitilis* encoding the reductive loop of module 1 was amplified by PCR using the following synthetic oligonucleotides as primers: 5'-CCTAGATCCGCCCACCTACCCCTTCCAACACCAG-3' (SEQ ID NO: 26) and 5'-TGGGCTAGCGTTTTGTGCAACTCCGCCGGTGGAGTG-3' (SEQ ID NO: 27) and as template either plasmid pIG155, which contains the first two modules of the avermectin PKS cloned into plasmid pT7-7, or chromosomal DNA of *Streptomyces* avermitilis. The PCR product was treated with T4 polynucleotide kinase and then ligated with plasmid pUC18, which had been linearised by digestion with SmaI and then treated with alkaline phosphatase. The ligation mixture was used to transform electrocompotent *E. coli* DH10B cells and individual colonies were checked for their plasmid content. The desired plasmid pIG67 was identified by its restriction pattern and by DNA sequencing.

Construction of Plasmid pJLK30

Plasmid pIG67 was digested with BglII and NheI and the 1.7 kbp fragment was ligated with plasmid pJLK117 which had been digested with BglII and NheI. The ligation mixture was used to transform electrocompetent *E. coli* DH10B cells and individual colonies were checked for their plasmid content. The desired plasmid pJLK30 was identified by its restriction pattern.

Example 30

Use of Plasmid pJLK30 for the Construction of *S. erythraea* JC2/pJLK30 and the Production of Triketides.

Approximately 5 mg of plasmid pJLK30 were used to transform protoplasts of *S. erythraea* JC2 and stable thiostrepton resistant colonies were isolated. From several colonies total DNA was obtained and analysed by Southern blot hybridisation to confirm that the plasmid had integrated into the TE. *S. erythraea* JC2/pJLK30 was plated onto SM3 agar containing 50 mg/ml thiostrepton and allowed to grow for twelve days at 30° C. 1 $cm^2$ of the plate was homogenized and extracted with a mixture of 1.2 ml ethyl acetate with 20 ml formic acid. The solvent was decanted and evaporated. The residue was dissolved in methanol and analysed by GC/MS and electrospray mass spectroscopy. The major products were identified as (2R, 3R, 4S, 5R)-5,3-dihydroxy-2,4-dimethyl-n-hexanoic acid δ-lactone and as (2R, 3R, 4S, 5R)-5,3-dihydroxy-2,4-dimethyl-n-heptanoic acid δ-lactone (total of 25 mg/l) Almost none of the corresponding 3-ketolactone could be detected.

Example 31

Construction of Plasmid pGMS2 pGMS2 is a pJLK117 based plasmid except that the DNA encoding the reductive loop of module 1 of the avermectin PKS has been inserted into the polylinker using the restriction sites PstI and Bsu36I. It was constructed via several intermediate plasmids.

Construction of Plasmid pIG68

The approximately 1.7 kbp DNA segment of the gene of the avermectin PKS of *S. avermitilis* encoding the reductive loop of module 1 was amplified by PCR using the following synthetic oligonucleotides as primers: 5'-TGGCTGCAGAGCTCACAGCCGGGTGCCGGATCCGGTT-3' (SEQ ID NO: 28) and 5'-TTTCCTCAGGTCCGCCGGTGGAGTGGGGCGCTGGAC-3' (SEQ ID NO: 29) and as template either plasmid pIG155, which contains the first two modules of the avermectin PKS cloned into plasmid pT7-7, or chromosomal DNA of *Streptomyces* avermitilis. The PCR product was treated with T4 polynucleotide kinase and then ligated with plasmid pUC18, which had been linearised by digestion with SmaI and then treated with alkaline phosphatase. The ligation mixture was used to transform electrocompotent *E. coli* DH10B cells and individual colonies were checked for their plasmid content. The desired plasmid pIG68 was identified by its restriction pattern and by DNA sequencing.

Construction of Plasmid pGMS1

Plasmid pIG68 was digested with PstI and Bsu36I and the 1.7 kbp fragment was ligated with plasmid pJLK116 which had been digested with PstI and Bsu36I. The ligation mixture was used to transform electrocompetent *E. coli* DH10B cells and individual colonies were checked for their plasmid content. The desired plasmid PGMS1 was identified by its restriction pattern.

Construction of Plasmid pGMS2

Plasmid pGMS1 was digested with NdeI and XbaI and the approximately 11.5 kbp fragment was ligated with plasmid pCJR24 which had been digested with NdeI and XbaI. The ligation mixture was used to transform electrocompetent *E. coli* DH10B cells and individual colonies were checked for their plasmid content. The desired plasmid pGMS2 was identified by its restriction pattern.

Example 32

Use of Plasmid pGMS2 for the Construction of *S. erythraea* JC2/pGMS2 and the Production of Triketides.

Approximately 5 mg of plasmid pGMS2 were used to transform protoplasts of *S. erythraea* JC2 and stable thiostrepton resistant colonies were isolated. From several colonies total DNA was obtained and analysed by Southern blot hybridisation to confirm that the plasmid had integrated into the TE. *S. erythraea* JC2/pGMS2 was plated onto SM3 agar containing 50 $\mu$g/ml thiostrepton and allowed to grow for twelve days at 30° C. 1 $cm^2$ of the plate was homogenized and extracted with a mixture of 1.2 ml ethyl acetate with 20 ml formic acid. The solvent was decanted and evaporated. The residue was dissolved in methanol and analysed by GC/MS and electrospray mass spectroscopy. The products were identified as (2R, 3R, 4S, 5R)-5,3-dihydroxy-2,4-dimethyl-n-hexanoic acid 5-lactone and as (2R, 3R, 4S, 5R)-5,3-dihydroxy-2,4-dimethyl-n-heptanoic acid $\alpha$-lactone (total of 17 mg/l), and also a substantial amount of the corresponding 3-ketolactone (5.5 mg/l).

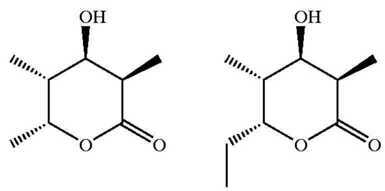

Example 33

Construction of Plasmid pJLK31 pJLK31 is a pJLK117 based plasmid except that the DNA encoding the reductive loop of module 2 of the avermectin PKS has been inserted into the polylinker using the restriction sites BglII and NheI. It was constructed via several intermediate plasmids.

Construction of Plasmid pIG69

The approximately 2.4 kbp DNA segment of the gene of the avermectin PKS of *S. avermitilis* encoding the reductive loop of module 2 was amplified by PCR using the following synthetic oligonucleotides as primers: 5'-CCTAGATCTC-CCCACCTACCCCTTCCAACACCACCACTACTG-3' (SEQ ID NO: 30) and 5'-CCGGCTAGCCGGGCGTG-CAGCTGGGCGCCGTTGTCCGCAC-3' (SEQ ID NO: 31) and as template either plasmid pIG155, which contains the first two modules of the avermectin PKS cloned into plasmid pT7-7, or chromosomal DNA of *Streptomyces* avermitilis. The PCR product was treated with T4 polynucleotide kinase and then ligated with plasmid pUC18, which had been linearised by digestion with SmaI and then treated with alkaline phosphatase. The ligation mixture was used to transform electrocompotent *E. coli* DH10B cells and individual colonies were checked for their plasmid content. The desired plasmid pIG69 was identified by its restriction pattern and by DNA sequencing.

Construction of Plasmid pJLK31

Plasmid pIG69 was digested with BglII, NheI and DraI and the 2.4 kbp fragment was ligated with plasmid pJLK117 which had been digested with BglII and NheI. The ligation mixture was used to transform electrocompetent *E. coli* DH10B cells and individual colonies were checked for their plasmid content. The desired plasmid pJLK31 was identified by its restriction pattern.

Example 34

Use of Plasmid pJLK31 for the Construction of *S. erythraea* JC2/pJLK31 and the Production of Triketides.

Approximately 5 mg of plasmid pJLK31 were used to transform protoplasts of *S. erythraea* JC2 and stable thiostrepton resistant colonies were isolated. From several colonies total DNA was obtained and analysed by Southern blot hybridisation to confirm that the plasmid had integrated into the TE. *S. erythraea* JC2/pJLK31 was plated onto SM3 agar containing 50 mg/ml thiostrepton and allowed to grow for twelve days at 30° C. 1 $cm^2$ of the plate was homogenized and extracted with a mixture of 1.2 ml ethyl acetate with 20 ml formic acid. The solvent was decanted and evaporated. The residue was dissolved in methanol and analysed by GC/MS and electrospray mass spectroscopy. The major products were identified as (2R, 3R, 4S, 5R)-5,3-dihydroxy-2,4-dimethyl-n-hexanoic acid 5-lactone and as (2R, 3R, 4S, 5R)-5,3-dihydroxy-2,4-dimethyl-n-heptanoic acid 5-lactone (total of 30 mg/liter).

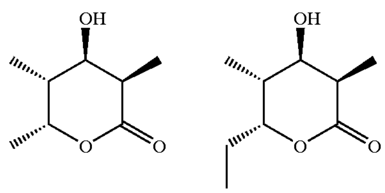

Example 35

Construction of Plasmid pGMS4

PGMS4 is a pJLK117 based plasmid except that the DNA encoding the reductive loop of module 2 of the avermectin PKS has been inserted into the polylinker using the restriction sites SnaBI and Bsu36I. It was constructed via several intermediate plasmids.

Construction of Plasmid pIG70

The approximately 2.4 kbp DNA segment the gene of the avermectin PKS of *S. avermitilis* encoding the reductive loop of module 2 was amplified by PCR using the following synthetic oligonucleotides as primers: 5'-CCCTACGTAC-CCCTTCCAACACCACTACTGGCTCGAAAG-3' (SEQ ID NO: 32) and 5'-GGCCCTCAGGTGGGCGCCGT-TGTCCGCACCACCGGTA-3' (SEQ ID NO: 33) as template either plasmid pIG155, which contains the first two modules of the avermectin PKS cloned into plasmid pT7-7, or chromosomal DNA of *Streptomyces* avermitilis. The PCR product was treated with T4 polynucleotide kinase and then ligated with plasmid pUC18, which had been linearised by digestion with SmaI and then treated with alkaline phosphatase. The ligation mixture was used to transform electrocompotent *E. coli* DH10B cells and individual colonies were checked for their plasmid content. The desired plasmid pIG70 was identified by its restriction pattern and by DNA sequencing.

Construction of Plasmid pGMS3

Plasmid pIG70 was digested with SnaBI, Bsu36I and DraI and the 2.4 kbp fragment was ligated with plasmid pJLK116 which had been digested with SnaBI and Bsu36I. The ligation mixture was used to transform electrocompetent *E. coli* DH10B cells and individual colonies were checked for their plasmid content. The desired plasmid PGMS3 was identified by its restriction pattern.

Construction of Plasmid PGMS4

Plasmid pGMS2 was digested with NdeI and XbaI and the approximately 12.4 kbp fragment was ligated with plasmid pCJR24 which had been digested with NdeI and XbaI. The ligation mixture was used to transform electrocompetent *E. coli* DH10B cells and individual colonies were checked for their plasmid content. The desired plasmid PGMS4 was identified by its restriction pattern.

Example 36

Use of Plasmid PGMS4 for the Construction of *S. erythraea* JC2/pGMS4 and the Production of Triketides.

Approximately 5 mg of plasmid pGMS4 were used to transform protoplasts of *S. erythraea* JC2 and stable thiostrepton resistant colonies were isolated. From several colonies total DNA was obtained and analysed by Southern blot hybridisation to confirm that the plasmid had integrated into the TE. *S. erythraea* JC2/pGMS4 was plated onto SM3 agar containing 50 mg/ml thiostrepton and allowed to grow for twelve days at 30° C. 1 $cm^2$ of the plate was homogenized and extracted with a mixture of 1.2 ml ethyl acetate with 20 ml formic acid. The solvent was decanted and evaporated. The residue was dissolved in methanol and analysed by GC/MS and electrospray mass spectroscopy. Only traces of putative triketide products were detected.

Example 37

Construction of Plasmid pJLK27

Plasmid pJLK27 is a pJLK114 based plasmid except that the DNA fragment encoding the reductive loop of module 13 of the rap PKS has been inserted into the mcs. It was constructed via several intermediate plasmids as follows.

Construction of Plasmid pJLK120a

The approximately 3.2 kbp DNA segment of the rapC gene of *S. hygroscopicus* encoding the reductive loop of module 13 was amplified by PCR using as primers the synthetic oligonucleotides: 5'-TACCTAGGCACCACCACAACCCGGGTA-3' (SEQ ID NO: 34) and 5'-TACAATTGGCCCGCGAGTCCCCGACGCT-3' (SEQ ID NO: 35) and cosmid cos 31 (Schwecke, T. et al. (1995) Proc. Natl. Acad. Sci. USA 92: 7839–7843) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK120a was identified by its restriction pattern and DNA sequencing.

Construction of Plasmid pJLK27

Plasmid pJLK120a was digested with AvrII and HpaI and the 3.2 kbp fragment was ligated with plasmid pJLK114 which had been digested with AvrII and HpaI. The ligation mixture was used to transform electrocompetent *E. coli* DH10B cells and individual colonies were checked for their plasmid content. The desired plasmid pJLK27 was identified by its restriction pattern.

Example 38

Use of Plasmid pJLK27 for Construction of JC2/pJLK27 and the Production of Triketides Approximately 5 mg plasmid pJLK27 were used to transform protoplasts of *S. erythraea* JC2 and stable thiostrepton resistant colonies were isolated. From several colonies total DNA was obtained and analysed by Southern blot hybridisation, to confirm that the plasmid has integrated into the TE. JC2/pJLK27 was plated onto SM3 agar containing 50 mg/ml thiostrepton and allowed to grow for twelve days at 30° C. 1 $cm^2$ (0.5 ml) of the plate was homogenised and extracted with a mixture of 1.2 ml ethyl acetate and 20 ml formic acid. The solvent was decanted and removed by evaporation and the residue dissolved in methanol and analysed by GC/MS and electrospray mass spectroscopy. The major products were identified (by comparison with authentic material) as (2R, 4S, 5R)-2,4-dimethyl-5-hydroxy-n-hexanoic acid δ-lactone and as (2R, 4S, 5R)-2,4-dimethyl-5-hydroxy-n-heptanoic acid δ-lactone (total of 41 mg/l), with some of the corresponding 3-ketolactones (total of 12 mg/l) and 3-hydroxylactones (total of 2.8 mg)

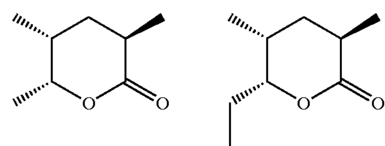

All documents and sequence deposits referred to herein are explicitly and individually incorporated herein by reference.

What is claimed is:

1. An isolated recombinant nucleic acid molecule encoding a Type I polyketide synthase (PKS) wherein said nucleic acid molecule is produced by:

a) providing a polynucleotide encoding at least an extension module of a PKS wherein said extension module contains at least one reductive domain;

b) deleting a portion of the polynucleotide which corresponds to said at least one reductive domain of said PKS; and c) replacing said deleted portion with a polylinker region having multiple restriction enzyme sites;

wherein said deleted portion corresponding to said at least one reductive domain is at least one domain selected from the group consisting of: a β-ketoreductase (KR) domain, a dehydratase (DH) domain and an enoyl reductase (ER) domain; wherein said polylinker is an in-frame addition to the PKS; and wherein said polylinker encodes a polypeptide.

2. A nucleic acid molecule according to claim 1 wherein the polylinker is inserted in place of all the nucleic acid sequences encoding reductive domains and which are naturally included in said extension module.

3. A nucleic acid according to claim 1, wherein said polylinker region connects a nucleic acid sequence encoding at least part of an acyl transferase domain to a nucleic acid sequence encoding at least part of an acyl carrier protein domain.

4. A nucleic acid molecule according to claim 1 wherein at least one of the restriction sites included in the polylinker is absent from the Type I polyketide synthase-encoding nucleic acid.

5. A nucleic acid molecule according to claim 1 wherein the polylinker includes at least one of the following restriction sites: AvrII; BglII; SnaBI; PstI; SpeI; NsiI; Bsu36I; NheI; and HpaI.

6. A nucleic acid molecule according to claim 1 which additionally encodes a loading module.

7. A nucleic acid molecule according to claim 1 which additionally encodes one or more further extension modules.

8. A nucleic acid molecule according to claim 1 further including a nucleic acid sequence incorporated into the polylinker, which incorporated nucleic acid encodes one or more replacement reductive domains, said one or more replacement reductive domains being selected from the group consisting of a β-ketoreductase (KR) domain, a dehydratase (DH) domain and an enoyl reductase (ER) domain.

9. A nucleic acid molecule according to claim 8 wherein said one or more replacement reductive domains include(s) at least a β-ketoreductase (KR).

10. A nucleic acid molecule according to claim 8 wherein at least one of said one or more replacement reductive domains is from a different extension module of said Type I polyketide synthase.

11. A nucleic acid molecule according to claim 8 wherein at least one of said one or more reductive domains is from a different polyketide synthase.

12. A vector including a nucleic acid as defined in claim 1.

13. A host cell transfected, transformed or conjugated with a nucleic acid as defined in claim 1.

14. A host cell according to claim 13 which is a cell of a *Streptomyces* species.

15. A host cell according to claim 14 which is a cell of *S. erythraea* or *S. avermitilis.*

16. A method for producing a nucleic acid encoding a novel polyketide synthase, the method including the steps of:

i. providing a nucleic acid molecule as defined in claim 1; and ii. incorporating into said polylinker a nucleic acid sequence which encodes at least one replacement reductive domain, said at least one replacement reductive domains being selected from the group consisting of a β-ketoreductase (KR) domain, a dehydratase (DH) domain and an enoyl reductase (ER) domain.

17. A method for producing a fermentation product containing a polyketide, the method including the step of culturing a host cell as defined in claim 13.

18. A method for producing a polyketide, the method including the steps of:

i. providing a fermentation product resulting from the method of claim 17; and ii. at least partially purifying a polyketide from said fermentation product.

19. A method according to claim 18 wherein the polyketide is an avermectin.

20. A method according to claim 19 wherein the avermectin is a $B_1$ avermectin.

21. A host cell transfected, transformed or conjugated with a vector as defined in claim 12.

22. A method according to claim 20, wherein the fermentation product of step (i) is substantially free of $B_2$ avermectins and wherein the recombinant nucleic acid molecule encoding the Type I polyketide synthase is a nucleic acid molecule encoding an avermectin polyketide synthase except that the ketoreductase domain of module 2 has been replaced with the ketoreductase domain and the dehydratase domain of module 10 of the rapamycin polyketide synthase.

23. An isolated or recombinant nucleic acid according to claim 1, wherein the polylinker region comprises the sequence of SEQ ID NO: 56.

24. An isolated or recombinant nucleic acid according to claim 1, wherein the polylinker region is selected from the group of polylinkers in plasmids pJLK114 and pJLK117.

* * * * *

SEQUENCE LISTING

```
<160> NUMBER OF SEQ ID NOS: 61

<210> SEQ ID NO 1
<211> LENGTH: 12381
<212> TYPE: DNA
<213> ORGANISM: Streptomyces avermitilis
```

-continued

<400> SEQUENCE: 1

```
cccgggcgat ctcccggatc acctgtgcgg ggctgggcat gtgcaggaga cactccaggg     60
cccacgccgc gtcgaaggac ccgtcgggaa acggcagttc catcgcgtcg gcacgggtga    120
acacgacccg gtccgccacg tgcgactgct tcgcgagagc ggtcgccagc ccgacctgaa    180
cctcgctcac cgtcacgccg acgacatcga cgggcgcgct cagggcgagc cgcaccgccg    240
gctttccgga accgcagccg acgtccagga cccggcggcc cgtgatgcct ctcagcttgc    300
cgatgaggag atcggtgagc cggtcggcgg ccttgcccgg tgaactgccg tcccccggct    360
gcggccagta tccgaggtgg gtgttcccac ccagcgcacg attcatgagg tcggtcaaac    420
ggtcgtagta gtcccccact tccagggaag agggcggggt ctgctccggg acggccatca    480
tggtcgggaa cctccgcaat ccgggccggg cggcccagct gtcgtggcga tctactccag    540
gaaacgtcga ccttttctg ccacttgtcc gagctatgca gacaccccga tcccctaaga     600
aatgaacacc cttgggaacg gcacagccca ggggtggata ggggtattcg ccgccgccgc    660
gccgtcatta gctttgaaga gttgaagacg ttcaagacat tgatgcccgg ccgtcagcgg    720
atttctcgcg ctcctttcat tcttcgacgc tgcattgcag ctctcatcat gtccgcacgg    780
ccgccgagca ttgcctagcg gtgaggacac agctcaggtg cagaggatgg acggcgggga    840
agaaccccgc cctgcggcag gggaggtcct cggagtggcc gacgaggcgg acggcggcgt    900
cgtcttcgtt tttcccgggc agggcccgca atggccgggc atgggaaggg aacttctcga    960
cgcttccgac gtcttccggg agagcgtccg cgcctgcgaa gccgcgttcg cgccctacgt   1020
cgactggtcg gtggagcagg tgttgcggga ctcgccggac gctcccgggc tggaccgggt   1080
ggacgtcgtc cagccgaccc tgttcgccgt catgatctcc ctggccgccc tctggcgctc   1140
gcaaggggtc gagccgtgcg cggtgctggg acacagcctg ggcgagatcg cggcagccca   1200
cgtctcggga ggcctgtccc tggccgacgc cgcacgcgtg gtgacgcttt ggagccaggc   1260
acagaccacc cttgccggga ccggcgcgct cgtctccgtc gccgccacgc cggatgagct   1320
cctgccccga atcgctccgt ggaccgagga caacccggcg cggctcgccg tcgcagccgt   1380
caacggaccc cggagcacag tcgtttccgg tgcccgcgag gccgtcgcgg acctggtggc   1440
cgacctcacc gccgcgcagg tgcgcacgcg catgatcccg gtggacgttc ccgcccactc   1500
cccccctgatg tacgccatcg aggaacgggt cgtcagcggc ctgctgccca tcaccccacg   1560
cccctcccgc atccccttcc actcctcggt gaccggcggc cgcctcgaca cccgcgagct   1620
agacgcggcg tactggtacc gcaacatgtc gagcacggtc cggttcgagc ccgccgcccg   1680
gctgcttctg cagcaggggc ccaagacgtt cgtcgagatg agcccgcacc cggtgctgac   1740
catgggcctc caggagctcg ccgcggacct gggcgacacc accggcaccg ccgacaccgt   1800
gatcatgggc acgctgcgcc gcggccaggg caccctggac cacttcctga cgtctctcgc   1860
ccaactacgg gggcatggtg agacgtcggc gaccaccgtc ctctcggcac gcctgaccgc   1920
gctgtccccc acgcagcagc agtcgctgct cctggacctg gtgcgcgccc acaccatggc   1980
ggtgctgaac gacgacggaa acgagcgcac cgcgtcggat gccggcccat cggcgagttt   2040
cgcccacctc ggcttcgact ccgtcatggg tgtcgaactg cgcaaccgcc tcagcaaggc   2100
cacgggcctg cggttgcccg tgacgctcat cttcgaccac accacgccgg ccgcggtcgc   2160
cgcgcgcctt cggaccgcgg cgctcggcca cctcgacgag gacaccgcgc ccgtaccgga   2220
ctcacccagc ggccacggag gcacggcagc ggcggacgac ccgatcgcca tcatcggcat   2280
ggcatgccgt ttcccgggcg gagtccggtc cccgaaggac ctgtgggagc tgcccgcctc   2340
```

-continued

```
gggcggagac gccatcgggc cgttccccac cgaccgcgga tggcccacgg aacagcgtca   2400
cgcccaggac cccacgcagc ccggcacgtt ctatccgcag ggaggcgggt tccttcacga   2460
cgcggcgcac ttcgacgccg gcttcttcgg aatcagtcca cgtgaggcac tggcgatgga   2520
tccgcagcag cggctgctgc tggagacgtc ctgggaggcg ttcgagcggg cgggaatcga   2580
tccgctgtcg gtacgcgggt cccgtacggg cgtcttcgcg ggcgccctct ccttcgacta   2640
cggcccgcgt atggacaccg cgtcgtcgga gggcgccgcg gacgtggagg gccacatcct   2700
caccggtacc acgggcagcg tcctgtcggg ccgtatcgcc tacagcttcg ggctggaagg   2760
gccggcgatc accgtggaca cggggtgctc ggcatcgctc gtgacgctgc atctggcgtg   2820
ccagtcgctg cggtcgggtg agtgcacgct cgcgctggcc ggcggcgtct cggtcatgtc   2880
caccctcggc atgttcatcg agttctcccg gcagcgcggg ctgtcggtgg acggcaggtg   2940
caaggcgtac tcggctgcag ccgacggcac cggctggggc gagggcgtcg ggatgctgtt   3000
ggtggagcgg ttgtcggatg cggtgcggct ggggcatcgg gtgctggcgg tggtacgcgg   3060
cagtgcggtc aaccaggacg gtgcgtcgaa tgggctgacg gcgccgaacg gtccggctca   3120
ggagcgggtg atccggcagg cgttggcgaa cgcggggttg tccgtggcgg atgtggatgt   3180
ggtggagggg cacgggacgg gcacgacgct gggtgatccg atcgaggcac aggcgttgct   3240
cgccacgtac gggcagcggg ccggtgacag gccgctgtgg ctggggtctc tgaagtccaa   3300
catcgggcac accatggctg ccgcgggtgt gggtggggtc atcaagatgg tgatggcgtt   3360
gcgggagggg gtgttgccgc ggacgttgca tgtggatgag ccgtcgccgc aggtggactg   3420
gtccgcgggg gcggtgcggc tgctgacgga ggcggtgccg tggccggggg acgcggcagg   3480
gcggttgcgg cgggcgggag tgtcgtcgtt cgggatcggc ggcacgaatg cgcatgtgat   3540
tttggaggag gcgccggcgg cgggggctg tgttgccggg ggtggggtgt tggagggtgc   3600
tccgggtctt gccatttcgg tggctgagtc ggtggccgct ccagtggctg tgtctgcgcc   3660
ggtggctgag tcggtgccgg tgccggtgcc ggtgccggtt cctgtgccgg tgtcggctag   3720
gtctgaggct gggttgcggg cgcaggcgga ggcgttgcgt cagtacgtgg cagtccggcc   3780
ggacgtttcg cttgccgatg tgggtgcggg tctggcctgt gggcgggctg tgctggagca   3840
tcgtgcggtc gtcctggccg cggaccgtga ggagctggtg caagggttgg gggcgctggc   3900
ggcgggtgag ccggatcggc gggtgaccac gggtcatgcg ccgggtggtg accggggcgg   3960
tgtcgtcttc gtgtttcccg gacagggtgg gcagtgggcc gggatgggtg tgcgtctgct   4020
cgcctcctct ccggtgttcg cccggcggat gcaggcgtgc gaggaggctc tggcgccgtg   4080
ggtggactgg tctgtggtgg acatcctgcg ccgggacgcg ggggatgcgg tgtgggagcg   4140
ggccgatgtg gtccagcctg tgctgttcag cgtcatggtg tctttggctg ctctgtggcg   4200
ttcctacggt atcgaacccg acgcggtcct tggccattcc cagggcgaga tcgcggccgc   4260
gcatgtgtgt ggggcgctga gcctgaagga cgcggcgaag actgttgcgc tgcgcagccg   4320
ggcgctggcc gctgtgcggg gccggggcgg catggcctca gtgccgctgc ctgcccagga   4380
ggtggagcag ctcattggtg agcggtgggc ggggcggttg tgggtggcgg cggtcaacgg   4440
cccccgctcc accgccgtct cgggggatgc cgaggcggtg gacgaggtgc tggcgtactg   4500
tgccggcacc ggggtgcggg cccggcggat cccggtcgac tatgcctcgc actgccccca   4560
tgtgcagccc ctgcgggagg agttgctgga gctgctgggg gacatcagcc cgcagccgtc   4620
cggcgtgccg ttcttctcca cggtggaggg cacctggctg gacaccacaa ccctggacgc   4680
```

-continued

```
cgcctactgg taccgcaacc tgcaccagcc ggtccgtttc agcgatgccg tccaggccct   4740
ggcggatgac ggacaccgcg tcttcgtcga agtcagcccc caccccaccc tcgtccccgc   4800
catcgaagac accaccgaag acaccgccga agacgtcacc gcgatcggca gcctccgccg   4860
cggcgacaac gacacccgcc gcttcctcac cgccctcgcc cacacccata ccaccggcat   4920
cggcacaccc accacctggc accaccacta cacccaccac cacacccacc cccaccccca   4980
cacgcacctc gacctgccca cctacccctt ccaacaccag cactactggc tcgagagctc   5040
acagccgggt gccggatccg gttcgggtgc cggtgccggt tcgggtgccg gttccgggcg   5100
ggcagggact gcgggcggga cggcagaggt ggagtcgcgg ttctgggacg cggtggcccg   5160
ccaggacctg gaaacggtcg cgaccacact cgccgtgccc ccctccgccg gcctggacac   5220
ggtggtgccc gcactctccg cctggcaccg ccaccaacac gaccaagccc gcatcaacac   5280
ctggacctac caggaaacct ggaaacccct caccctcccc accacccacc aaccccacca   5340
aacctggctc atcgccatcc ccgaaaccca gacccaccac ccccacatca ccaacatcct   5400
caccaacctc caccaccacg gcatcacccc catccccctc accctcaacc acacccacac   5460
caacccccaa cacctccacc acaccctcca ccacacccga caacaagccc aaaaccacac   5520
caccggagcc atcaccggcc tgctctccct cctcgccctc gacgaaacac cccaccccca   5580
ccacccccac acacccaccg gcaccctcct caacctcacc ctcacccaaa cccacaccca   5640
aacccaccca ccaacccccc tctggtacgc caccaccaac gccaccacca cccaccccaa   5700
cgacccccctc acacacccca cccaagccca aacctgggga ctcgcccgca ccaccctcct   5760
cgaacacccc acccacaccg ccggaatcat cgacctcccc accaccccca ccccccacac   5820
cctccaccac ctcacccaaa ccctcaccca accccaccac caaacccaac tcgccatccg   5880
caccaccggc acccacaccc gccgcctcac ccccaccacc ctcaccccca cacaccaacc   5940
acccaccccc accccccacg gaaccaccct catcaccggc ggaaccggcg ccctcgccac   6000
ccacctcacc caccacctca ccacccacca acccacccaa cacctcctcc tcaccagccg   6060
aaccggcccc cacaccccc acgcacaaca cctcaccacc caactccaac aaaaaggcat    6120
ccacctcacc atcaccacct gcgacaccag caacccagac caactccaac atctcctcaa   6180
caccatcccc ccacaacacc ccctcaccac cgtcatccac accgcaggca tcctcgacga   6240
cgccaccctc accaacctca cccccaccca actcaacaac gtcctccgcg ccaaagccca   6300
cagcgcccac ctcctccacc aactcaccca acacaccccc ctcaccgcct tcgtcctcta   6360
ctcctccgcc gccgccacct tcggcgcacc cggccaagcc aactacgccg cagccaacgc   6420
ctacctcgac gccctcgccc accaccgcca cacccaccac ctccccgcca ccagcatcgc   6480
ctggggcacc tggcaaggaa acggactcgc tgattcggac aaggcccgcg catatctcga   6540
ccgccgcggg tttcgaccca tgtcacccga gttggccacg gcagcggtca cgcaggcgat   6600
cgcggacacc gaacggccgt atgtcgtcat cgccgacatc gactggagca agatcgaaca   6660
cacctctcag accagcgacc tggtgagcgc ggcccgggaa agggagccag ctgtccagcg   6720
ccccactcca ccggcggagt tgcacaaaac gctggcccat cagacgtcgg ccgaccaacg   6780
ggccgcattg ctcgagctcg tacgagacca tgtggcggca gtgctccggc acgcggaccc   6840
gaaagccatc gcgcccgacc agtcgttccg tgcactcggc ttcgattcac tcacggccgt   6900
cgagttccga aacctgctga tcaaggcaac aggactccgc cttcctgtct cgctggtctt   6960
cgaccacccg acccctgcca aactcgccgt acacctgcag aaccaactgc ggggcacagc   7020
agcggagtcg gctccttcag cggcagccgt taccgccgag gcttctgtca ccgagccgat   7080
```

-continued

```
cgccatcgtt ggcatggcct gtcgtttccc cggcggagtg acctcggcgg acgacttctg   7140
ggatctgatc tcctccgagc aggacgcgat cggcggattc cccaccgacc gcggctggga   7200
cctggacacg ctctacgacc ccgaccccga ccaccccggc acctgctaca cccgaaacgg   7260
cggattcctc tacgacgcag gccacttcga cgccgaattc ttcggcatca gcccccgcga   7320
agccctcgcc atggaccccc agcaacgact cctcctcgaa accgcctggg aaaccatcga   7380
acacgccggc atcaaccccc acaccctcca cggcaccccc accggagtct tcaccggcac   7440
caacggacag gactacgcac ttcgcgtgca caacgcgggc cagtcaaccg atggtttcgc   7500
actgaccgga accgccggca gcgtcatctc cggtcgtatc tcgtacacgt ttggttttga   7560
gggtcctgcg gtgtcggtgg acacggcttg ttcctcgtcg ttggtggctt tgcatctggc   7620
ctgtcaggcg ttgcgtgcgg gtgagtgctc gatggcgctt gccgggggtg tgacggtgat   7680
gtcgtctccg ggtgccttcg tggagttttc gcggcagcgg ggtctggccg cggacgggca   7740
ttgcaaggcg ttctcggcgg cggcggacgg gaccggctgg ggtgagggtg tggggatgct   7800
gctggtggag cggctctccg acgcccatcg caacggtcac cgtgtcctgg ccgtggtgcg   7860
tggcagtgcg gtcaaccagg acggtgcgag caacggtctg accgcgccca acgggccgtc   7920
ccagcagcgt gtcatccgcc aggccctcgc caacgccggc ttgtcggccg gtgatgtcga   7980
cgcggtggag gcccacggca ccggcaccac tttgggcgac ccgatcgagg cccaggccct   8040
cctcgcgacc tacggacagg accgtgccgg cgagggggccg ctgtggctgg gctcggtcaa   8100
gtccaatgtc ggtcacacac aggctgccgc gggcgtcgcc ggggtgatca agatggtgat   8160
ggcgctgcgg catggtctgc tgccgcggac gttgcatgtg gatgagccgt cgccgcatgt   8220
ggactggtcc gcgggtgcgg tgcagctgct gacggagacg gtgccctggc ccggcgggga   8280
ggggcggcta cggcgggcag gagtgtcatc attcggcgtc agcggcacca acgcccacgt   8340
catcctcgaa gaagcacccg ccgacgacgt tccgggggga ccacccgccg gcgagggtga   8400
cgcgggcagc gacgatgagg ctgctgccgg cagtcctggg gtgtggccgt ggctggtgtc   8460
ggccaagtcg cagccggccc tgcgcgccca ggcccaggcc ctgcacgccc acctcaccga   8520
ccaccccggc ctcgacctcg cggatgtcgg atacaccctc gcccacgccc gcgccgtgtt   8580
cgaccaccgc gccaccctca tcgccgcgga ccgcgacacg ttcctgcaag cactccaggc   8640
actcgccgca ggcgagcccc accccgccgt catccacagc agcgccccgg gcgggaccgg   8700
gaccggggag gccgcaggaa agaccgcatt catctgctcc ggacagggca cccaacgccc   8760
cggcatggcc cacggcctct accacaccca ccccgtcttc gccgccgcac tcaacgacat   8820
ctgcacccac ctcgaccccc acctcgacca ccccctcctc cccctcctca cccaaaacga   8880
caacgacaac gaggacgcgg ccgcactgct ccagcagacc cgctacgccc agcccgccct   8940
cttcgccttc caggtcgccc tccaccgcct cctcaccgac ggctaccaca tcaccccccca   9000
ctactacgcc ggacactccc tcggcgaaat caccgccgcc cacctcgccg gcatcctcac   9060
cctcaccgac gccaccaccc tcatcaccca acgcgccacc ctcatgcaaa ccatgccccc   9120
cggcaccatg accaccctcc acaccacccc ccaccacatc acccaccacc tcaccgccca   9180
cgaaaacgac ctcgccatcg ccgccatcaa caccccccacc tccctcgtca tcagcggcac   9240
cccccacacc gtccaacaca tcaccaccct ctgccaacaa caaggcatca aaaccaaaac   9300
cctccccacc aaccacgcct tccactcccc ccacaccaac cccatcctca accaactcca   9360
ccagcacacc caaaccctca cctaccaccc accccacacc cccctcatca ccgacaacac   9420
```

-continued

```
cccacccgac caactcctca ccccccacta ctggacccaa caagcccgca acaccgtcga    9480
ctacgccacc accacccaaa ccctccacca acacggcgtc accacctaca tcgatctcgg    9540
acccgacaac accctcacca ccctcaccca ccacaacctc cccaacaccc ccaccaccac    9600
cctcaccctc acccaccccc accaccaccc ccaaacccac ctcctcacca acctcgccaa    9660
aaccaccacc acctggcacc cccaccacta cacccaccac cacaaccaac cccacaccca    9720
cacccacctc gacctcccca cctacccctt ccaacaccac cactactggc tcgaaagcac    9780
acagcccggt gccggcaacg tgtcagcagc cggactcgac ccccaccgaac accccctact    9840
cggcgccaca ttggaactgg cgactgacgg tggagcgctt cttgcagggc gcttgtcttt    9900
gaggtcgcat ccgtggctgg ctgaccatgc cgtcggcggc acggtgctgc tgtcgggcgc    9960
caccttcctc gaactcgccc ttcatgcggg cacatacgtg ggctgcgacc gagtggatga   10020
gctgacgctg catgcgccgc tggtggttcc tgtggatggg ggtgtgagtg tgcaggttgg   10080
ggttgcggct gcggatgggg aggggcggcg tttggtgagt gtgtatgcgc ggggtgggag   10140
tgcttgtggt gggggtggtg cgtcgggtgg ggtgtggacg tgtcatgcct cgggggtgct   10200
ggttgaggct gctgctggtg gtgtggtggt ggatggtctg gcgggggtgt ggccgccgcg   10260
gggtgcggtg gcggtggatg tcgatggtgt ccgtgaccgt ttggctgggg ctggttgtgt   10320
tttggggccg gtgttttcgg ggctgcgtgc ggtgtggcgt gatgggggg atttgctggc   10380
tgaggtgtgt ctgccggagg aggcgtgggg tgatgcggct ggttttgggc tgcatccggc   10440
gttgctggat ggtgtggtcc agccgttgtc ggtgttgctt ccgggtggga cggggtttgg   10500
ggagggggcg gggttcgggg agggtgttcg ggtgccggct gtgtggggtg gtgtgtcgct   10560
tcaccgggcg ggtgtgaccg gtgtgcgggt gcgtgtgtcg gctgtcgggc ggggcggcgg   10620
gcgtgaggcg gtgtcggtcg tggtcgggga tgaggcgggt gtgccggtgg cgtcggtcga   10680
tcgtcttgag ttgcggcctg tggatatggg tcagttgcgt gctgtctcgg tttcggcggg   10740
gcggcggggt tcgctgtatg cggtgcagtg ggctgaggtg ggtcctgtgc cggtgtgtgg   10800
gcaggcgtgg gcgtggcacg aggacgtggg tgagagcggt ggtgggcctg tgccgggggt   10860
ggtggtgttg cggtgcccgg atgccggtgc cggtggcggt ggcggtggcg gtggtggcgg   10920
tggtgtgggt gaggttgttg gtggggtgtt gggtgtggtg caggggtggc tggggctgga   10980
gcggtttgcg ggttcgcggc tggtggtggt gacccggggt gcggtggtgg ccggcccgga   11040
ggacggcccg gtggatgtgg tgggtgcgtc ggtgtggggg ctggtgcgtt cggcgcaggc   11100
tgagcatccg gaccggtttg tcctcctcga cctcgacacc gacaccggca ccgacctcga   11160
caccggtgct ggtgctggtt ggggcgtgga tggtgggcgt gtggcggcgg tggtggcgtg   11220
tggtgagccg cagttggcgg tgcgtgggga gcggttgctg gccgcacgcc tgacacgact   11280
tgagtcatcc ggtgatgttc cagcccagcg gtccggtgac acacgagccc ggcggtccga   11340
cgtgcctgcc cagcgctccg gtggcgtgcc tgctcggcgg tcggttgatg tatcgggtcg   11400
ggaggtgttg ccgtggttgt cgggtgggtc ggtgttggtg acgggtggga cgggtgtgct   11460
gggtgcggcg gtggcgcggc atctggctgg tgtgtgtggg gtgcgggatc tgctgttggt   11520
gagccggcgt ggtccggatg ctccgggtgc ggagggtctg cgggcggagc tggccgcgtt   11580
gggggcggag gtgcggattg ttgcgtgtga tgtgggggag cggcgggagg tggtccggct   11640
gctggagggt gttcctgccg ggtgtccgct gacgggtgtc gtgcatgcgg ctggtgtgct   11700
ggacgatgcg acgatcgcct ctctcacgcc cgagcggctg ggcacggtgt tcgcggccaa   11760
ggtggatgcc gctcttttgc tggatgagct gacgcggggt atggagctgt cggcgttcgt   11820
```

gctgttctcc tcggccgcgg ggatcctggg gtcggccggg cagggcaact acgccgcggc 11880
caatgccgct ctggacgcgc tggcgtaccg gcggcgggcg gcgggtctgc cgggggtgtc 11940
gctggcgtgg gggctgtggg aagaggccag cgggatgacc gggcacctgg ccggcaccga 12000
ccaccggcgc atcatccgtt ccggtctgca tcccatgtcg accccggacg cactggccct 12060
cttcgatgcg gccctggctc tggaccggcc ggtcctgctg cccgccgacc tgcgtcccgc 12120
cccgcccctg ccgcccctgc tgcaggacct cctgcccgcc acccgccgcc gcaccacccg 12180
caccaccact accggtggtg cggacaacgg cgcccagctg cacgcccggc tggccggcca 12240
gacacacgaa caacagcaca ccaccctcct cgccctggtc cgctcccaca tcgccaccgt 12300
cctgggccac accacccccg acaccatccc ccccgaccgc gcgttccgcg acctcggctt 12360
cgactccctc accgccgtcg a 12381

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
tacctaggcc gggccggact ggtcgacctg ccgggtt 37

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
atgttaaccg gtcgcgcagg ctctccgtct 30

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
atgttaacgg gtctgccgcg tgccgagcgg ac 32

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
cttctagact atgaattccc tccgcccagc 30

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6

```
atactagtcc tcgtgacgag ctcgacgg                                  28


<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7

taatgcatcc ggttctccgg cccgctcgct                                30


<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8

taagatcttc cgacctacgc cttccaac                                  28


<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9

taatgcatcg acctcgttgc gtgccgcggt                                30


<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10

atagatctgc ctacgtaccc gttcgaacac cagcgcttc                      39


<210> SEQ ID NO 11
<211> LENGTH: 50
<212> TYPE: DNA
<213> ORGANISM: Artificial Sequence
<220> FEATURE:
<223> OTHER INFORMATION: Primer

<400> SEQUENCE: 11

atcctcaggt tcggccctgc cgcctcggcc tgcccggcgg cgcgcagctt          50


<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12

taagatcttc cgacgtacgc gttccagc                                  28


<210> SEQ ID NO 13
<211> LENGTH: 33
<212> TYPE: DNA
<213> ORGANISM: Artificial Sequence
```

<220> FEATURE:
<223> OTHER INFORMATION: Primer

<400> SEQUENCE: 13
atgctagcca ctgcgccgac gaatcaccgg tgg 33

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
taagatctcc ctacgtaccc cttcaaccac 30

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
gctagccgcc gcgccagctc gggc 24

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
cctacgtacg ccttcgacca ccagcactt 29

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
cggctagcgg gcgttccagg ccgccgtcct 30

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
tacctgaggg accggctagc gggtctgccg cgtg 34

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
atgctagccg ttgtgccggc tcgccggtcg gtcc 34

-continued

<210> SEQ ID NO 20
<211> LENGTH: 34
<212> TYPE: DNA
<213> ORGANISM: Artificial Sequence
<220> FEATURE:
<223> OTHER INFORMATION: Primer

<400> SEQUENCE: 20
gacgccgaat tcttcggcat cagccccgc gaag 34

<210> SEQ ID NO 21
<211> LENGTH: 63
<212> TYPE: DNA
<213> ORGANISM: Artificial Sequence
<220> FEATURE:
<223> OTHER INFORMATION: Primer

<400> SEQUENCE: 21
gagctagcag gtggggagat ctaggtgggt gtgggtgtgg ggttggttgt ggtggtgggt 60
gta 63

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
gcccggctag ccggccagac acacgaacaa cagc 34

<210> SEQ ID NO 23
<211> LENGTH: 34
<212> TYPE: DNA
<213> ORGANISM: Artificial Sequence
<220> FEATURE:
<223> OTHER INFORMATION: Primer

<400> SEQUENCE: 23
gggaattcct cgaggatgac gtgggcgttg gtgc 34

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
taagatctag cgctccgagg ttcttgcccg 30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
atgctagcct accgctgccc gggtccgccg 30

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26
cctagatccg cccacctacc ccttccaaca ccag 34

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
tgggctagcg ttttgtgcaa ctccgccggt ggagtg 36

<210> SEQ ID NO 28
<211> LENGTH: 37
<212> TYPE: DNA
<213> ORGANISM: Artificial Sequence
<220> FEATURE:
<223> OTHER INFORMATION: Primer

<400> SEQUENCE: 28
tggctgcaga gctcacagcc gggtgccgga tccggtt 37

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
tttcctcagg tccgccggtg gagtggggcg ctggac 36

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
cctagatctc cccacctacc ccttccaaca ccaccactac tg 42

<210> SEQ ID NO 31
<211> LENGTH: 40
<212> TYPE: DNA
<213> ORGANISM: Artificial Sequence
<220> FEATURE:
<223> OTHER INFORMATION: Primer

<400> SEQUENCE: 31
ccggctagcc gggcgtgcag ctgggcgccg ttgtccgcac 40

<210> SEQ ID NO 32
<211> LENGTH: 39
<212> TYPE: DNA
<213> ORGANISM: Artificial Sequence
<220> FEATURE:
<223> OTHER INFORMATION: Primer

<400> SEQUENCE: 32
ccctacgtac cccttccaac accactactg gctcgaaag 39

<210> SEQ ID NO 33
<211> LENGTH: 37
<212> TYPE: DNA
<213> ORGANISM: Artificial Sequence
<220> FEATURE:
<223> OTHER INFORMATION: Primer

<400> SEQUENCE: 33
ggccctcagg tgggcgccgt tgtccgcacc accggta 37

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
tacctaggca ccaccacaac ccgggta 27

<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35
tacaattggc ccgcgagtcc ccgacgct 28

<210> SEQ ID NO 36
<211> LENGTH: 35
<212> TYPE: PRT
<213> ORGANISM: Streptomyces erythraea

<400> SEQUENCE: 36

```
Val Ala Val Asp Trp Glu Ala Val Leu Gly Arg Ala Gly Leu Val Asp
 1               5                  10                  15

Leu Pro Gly Tyr Pro Phe Gln Gly Lys Arg Phe Trp Leu Leu Pro Asp
            20                  25                  30

Arg Thr Thr
        35
```

<210> SEQ ID NO 37
<211> LENGTH: 35
<212> TYPE: PRT
<213> ORGANISM: Streptomyces erythraea

<400> SEQUENCE: 37

```
Val Thr Thr Ala Pro Ser Glu Arg Ala Gly Glu Pro Glu Thr Glu Ser
 1               5                  10                  15

Leu Arg Asp Arg Leu Ala Gly Leu Pro Arg Ala Glu Arg Thr Ala Glu
            20                  25                  30

Leu Val Arg
        35
```

<210> SEQ ID NO 38
<211> LENGTH: 41
<212> TYPE: PRT
<213> ORGANISM: Streptomyces erythraea

<400> SEQUENCE: 38

```
Val Ala Val Asp Trp Glu Ser Val His Leu Gly Thr Gly Ala Arg Arg
```

-continued

```
 1               5                   10                  15

Val Pro Leu Pro Thr Tyr Pro Phe Gln Arg Glu Arg Val Trp Leu Glu
            20                  25                  30

Pro Lys Pro Val Ala Arg Arg Ser Thr
        35                  40


<210> SEQ ID NO 39
<211> LENGTH: 33
<212> TYPE: PRT
<213> ORGANISM: Streptomyces erythraea

<400> SEQUENCE: 39

Asp Asp Ala Arg Arg Ala Ala Pro Gly Ala Pro Ala Glu Pro Arg Val
 1               5                   10                  15

Gly Ala Leu Ala Ser Leu Pro Ala Pro Glu Arg Glu Glu Ala Leu Phe
            20                  25                  30

Glu


<210> SEQ ID NO 40
<211> LENGTH: 41
<212> TYPE: PRT
<213> ORGANISM: Streptomyces erythraea

<400> SEQUENCE: 40

Val Gly Ala Asp Leu Arg Pro Ala Val Ala Gly Gly Arg Pro Ala Glu
 1               5                   10                  15

Leu Pro Thr Tyr Pro Phe Glu His Gly Arg Phe Trp Pro Arg Pro His
            20                  25                  30

Arg Pro Ala Asp Val Ser Ala Leu Gly
        35                  40


<210> SEQ ID NO 41
<211> LENGTH: 35
<212> TYPE: PRT
<213> ORGANISM: Streptomyces erythraea

<400> SEQUENCE: 41

Arg Ala Lys Leu Arg Ala Ala Gly Gly Ala Glu Ala Ala Gly Pro Asn
 1               5                   10                  15

Val Val Asp Arg Leu Ala Gly Arg Ser Glu Ser Asp Gln Val Ala Gly
            20                  25                  30

Leu Ala Glu
        35


<210> SEQ ID NO 42
<211> LENGTH: 38
<212> TYPE: PRT
<213> ORGANISM: Streptomyces erythraea

<400> SEQUENCE: 42

Val Glu Val Asp Trp Ser Pro Ala Phe Ala Asp Ala Arg Pro Val Glu
 1               5                   10                  15

Leu Pro Val Tyr Pro Phe Gln Arg Gln Arg Tyr Trp Leu Pro Ile Pro
            20                  25                  30

Thr Gly Gly Arg Ala Arg
        35


<210> SEQ ID NO 43
<211> LENGTH: 34
<212> TYPE: PRT
```

<213> ORGANISM: Streptomyces erythraea

<400> SEQUENCE: 43

Ala Gly Ala Arg Ala Glu Ala Arg Gln Ser Glu Glu Gly Pro Ala Leu
1 5 10 15

Ala Gln Arg Leu Ala Ala Leu Ser Thr Ala Glu Arg Arg Glu His Leu
20 25 30

Ala His

<210> SEQ ID NO 44
<211> LENGTH: 40
<212> TYPE: PRT
<213> ORGANISM: Streptomyces hygroscopius

<400> SEQUENCE: 44

Val Thr Val Asp Trp Pro Ala Ile Leu Gly Thr Thr Thr Ala Arg Val
1 5 10 15

Leu Asp Leu Pro Thr Tyr Ala Phe Gln His Gln Arg Tyr Trp Val Lys
20 25 30

Ser Val Asp Arg Ala Ala Ala Asp
35 40

<210> SEQ ID NO 45
<211> LENGTH: 32
<212> TYPE: PRT
<213> ORGANISM: Streptomyces hygroscopicus

<400> SEQUENCE: 45

Arg Pro Ile Ala Arg Arg Ala Ala Ser Thr Gly Asp Ser Ser Val Gln
1 5 10 15

Trp Leu Ala Ala Leu Ala Pro Glu Glu Arg Ala Lys Ala Leu Leu Arg
20 25 30

<210> SEQ ID NO 46
<211> LENGTH: 40
<212> TYPE: PRT
<213> ORGANISM: Streptomyces hygroscopicus

<400> SEQUENCE: 46

Val Thr Val Asp Trp Pro Ala Ile Leu Gly Thr Ala Thr Thr Arg Val
1 5 10 15

Pro Asp Leu Pro Thr Tyr Ala Phe Gln His Gln Arg Phe Trp Ala Glu
20 25 30

Gly Ala Asp Arg Ser Val Ala Gly
35 40

<210> SEQ ID NO 47
<211> LENGTH: 32
<212> TYPE: PRT
<213> ORGANISM: Streptomyces hygroscopicus

<400> SEQUENCE: 47

Arg Pro Val Ala Arg Arg Ala Ala Ser Thr Gly Gly Ser Ser Val Gln
1 5 10 15

Trp Leu Ala Arg Leu Ala Pro Val Glu Arg Glu Lys Ala Leu Leu Lys
20 25 30

<210> SEQ ID NO 48
<211> LENGTH: 44
<212> TYPE: PRT
<213> ORGANISM: Streptomyces hygroscopicus

```
<400> SEQUENCE: 48

Val Thr Val Asp Trp Arg Ala Val Leu Gly Asp Val Pro Ala Thr Arg
 1               5                  10                  15

Val Leu Asp Leu Pro Thr Tyr Ala Phe Gln His Gln Arg Tyr Trp Ala
            20                  25                  30

Glu Ala Gly Arg Ser Ala Asp Val Ser Ala Ala Gly
        35                  40


<210> SEQ ID NO 49
<211> LENGTH: 32
<212> TYPE: PRT
<213> ORGANISM: Streptomyces hygroscopicus

<400> SEQUENCE: 49

Arg Pro Val Ala Arg Arg Ala Ala Ser Thr Gly Asp Ser Ser Ala Gln
 1               5                  10                  15

Trp Leu Val Gly Leu Ala Pro Glu Glu Arg Ala Lys Ala Leu Leu Lys
            20                  25                  30


<210> SEQ ID NO 50
<211> LENGTH: 40
<212> TYPE: PRT
<213> ORGANISM: Streptomyces hygroscopicus

<400> SEQUENCE: 50

Val Thr Val Asp Trp Pro Ala Ile Leu Gly Thr Thr Thr Thr Arg Val
 1               5                  10                  15

Leu Asp Leu Pro Thr Tyr Ala Phe Gln His Gln Arg Tyr Trp Leu Lys
            20                  25                  30

Ser Val Asp Arg Ala Ala Ala Asp
        35                  40


<210> SEQ ID NO 51
<211> LENGTH: 35
<212> TYPE: PRT
<213> ORGANISM: Streptomyces hygroscopicus

<400> SEQUENCE: 51

Arg Pro Gln Ser Arg Thr Ala Ala Arg Asn Glu Val Gly Ser Gln Pro
 1               5                  10                  15

Leu Ser Ala Arg Leu Thr Gly Arg Thr Ser Val Glu Gln His Arg Ile
            20                  25                  30

Met Leu Glu
        35


<210> SEQ ID NO 52
<211> LENGTH: 24
<212> TYPE: PRT
<213> ORGANISM: Streptomyces avermitilis

<400> SEQUENCE: 52

Thr His Pro His Pro His Thr His Leu Asp Leu Pro Thr Tyr Pro Phe
 1               5                  10                  15

Gln His Gln His Tyr Trp Leu Glu
            20


<210> SEQ ID NO 53
<211> LENGTH: 25
<212> TYPE: PRT
<213> ORGANISM: Streptomyces avermitilis
```

<400> SEQUENCE: 53

```
Pro Thr Pro Pro Ala Glu Leu His Lys Thr Leu Ala His Gln Thr Ser
 1               5                  10                  15

Ala Asp Gln Arg Ala Ala Leu Leu Glu
            20                  25
```

<210> SEQ ID NO 54
<211> LENGTH: 24
<212> TYPE: PRT
<213> ORGANISM: Streptomyces avermitilis

<400> SEQUENCE: 54

```
Asn Gly Pro His Thr His Thr His Leu Asp Leu Pro Thr Tyr Pro Phe
 1               5                  10                  15

Gly His His His Tyr Trp Leu Glu
            20
```

<210> SEQ ID NO 55
<211> LENGTH: 25
<212> TYPE: PRT
<213> ORGANISM: Streptomyces avermitilis

<400> SEQUENCE: 55

```
Ala Asp Asn Gly Ala Gly Leu His Ala Arg Leu Ala Gly Gln Thr His
 1               5                  10                  15

Glu Gln Gly His Thr Thr Leu Leu Ala
            20                  25
```

<210> SEQ ID NO 56
<211> LENGTH: 122
<212> TYPE: DNA
<213> ORGANISM: Artificial Sequence
<220> FEATURE:
<223> OTHER INFORMATION: Synthetic oligonucleotide

<400> SEQUENCE: 56

```
ctaggccggg ccggactggt agatctgcct acgtatcctt tccagggcaa gcggttctgg     60

ctgcagccgg accgcactag tcctcgtgac gagggagatg catcgagcct gagggaccgg    120

tt                                                                   122
```

<210> SEQ ID NO 57
<211> LENGTH: 118
<212> TYPE: DNA
<213> ORGANISM: Artificial Sequence
<220> FEATURE:
<223> OTHER INFORMATION: Synthetic oligonucleotide

<400> SEQUENCE: 57

```
aaccggtccc tcaggctcga tgcatctccc tcgtcacgag gactagtgcg gtccggctgc     60

agccagaacc gcttgccctg gaaaggatac gtaggcagat ctaccagtcc ggcccggc      118
```

<210> SEQ ID NO 58
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 58

```
ctaggccggg ccggactggt agatctgcct acgtatcctt tccagggcaa gcggttctgg     60
```

-continued

```
ctgcag                                                                  66


<210> SEQ ID NO 59
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 59

ctgcagccag aaccgcttgc cctggaaagg atacgtaggc agatctacca gtccggcccg      60

gc                                                                      62


<210> SEQ ID NO 60
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 60

ccggaccgca ctagtcctcg tgacgaggga gatgcatcga gcctgaggga ccggtt          56


<210> SEQ ID NO 61
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 61

aaccggtccc tcaggctcga tgcatctccc tcgtcacgag gactagtgcg gtccgg          56
```